US010690676B2

(12) United States Patent
Barnidge et al.

(10) Patent No.: US 10,690,676 B2
(45) Date of Patent: Jun. 23, 2020

(54) QUANTIFYING MONOCLONAL ANTIBODY THERAPEUTICS BY LC-MS/MS

(71) Applicant: Mayo Foundation for Medical Education and Research, Rochester, MN (US)

(72) Inventors: David R. Barnidge, Rochester, MN (US); Maria Alice Vieira Willrich, Rochester, MN (US); David L. Murray, Rochester, MN (US); Melissa R. Snyder, Rochester, MN (US)

(73) Assignee: Mayo Roundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/329,512

(22) PCT Filed: Jul. 29, 2015

(86) PCT No.: PCT/US2015/042580
§ 371 (c)(1),
(2) Date: Jan. 26, 2017

(87) PCT Pub. No.: WO2016/018978
PCT Pub. Date: Feb. 4, 2016

(65) Prior Publication Data
US 2018/0106815 A1    Apr. 19, 2018

Related U.S. Application Data

(60) Provisional application No. 62/030,493, filed on Jul. 29, 2014.

(51) Int. Cl.
*G01N 33/68* (2006.01)
*A61K 39/395* (2006.01)

(52) U.S. Cl.
CPC ..... *G01N 33/6848* (2013.01); *A61K 39/3955* (2013.01); *G01N 33/6854* (2013.01); *G01N 2800/52* (2013.01)

(58) Field of Classification Search
None
See application file for complete search history.

(56) References Cited

U.S. PATENT DOCUMENTS

| 8,501,907 B2 | 8/2013 | Jordan et al. |
| 8,679,767 B2 | 3/2014 | Kaur et al. |
| 2002/0182649 A1 | 12/2002 | Weinberger et al. |

(Continued)

FOREIGN PATENT DOCUMENTS

| WO | WO 2006/138629 | 12/2006 |
| WO | WO 2013096451 | 6/2013 |

(Continued)

OTHER PUBLICATIONS

Wine, Y. et al. Molecular deconvolution of the monoclonal antibodies that comprise the polyclonal serum response, PNAS vol. 110, No. 8, pp. 2993-2998 (Year: 2013).*

(Continued)

*Primary Examiner* — Xiaoyun R Xu
(74) *Attorney, Agent, or Firm* — Fish & Richardson P.C.

(57) ABSTRACT

This document relates to methods for quantifying antibody therapeutics using mass spectrometry techniques.

18 Claims, 8 Drawing Sheets

(56) References Cited

U.S. PATENT DOCUMENTS

| | | |
|---|---|---|
| 2003/0027216 A1 | 2/2003 | Kiernan et al. |
| 2005/0009009 A1 | 1/2005 | Peiris et al. |
| 2005/0064422 A1 | 3/2005 | Barnidge et al. |
| 2006/0024296 A1 | 2/2006 | Williams et al. |
| 2006/0281122 A1 | 12/2006 | Bryant |
| 2007/0184470 A1 | 8/2007 | Aman et al. |
| 2007/0259398 A1 | 11/2007 | Arnott et al. |
| 2007/0292441 A1 | 12/2007 | Glover et al. |
| 2008/0064055 A1 | 3/2008 | Bryant |
| 2008/0142696 A1 | 6/2008 | Geromanos et al. |
| 2008/0317745 A1 | 12/2008 | Boruchov et al. |
| 2009/0186423 A1 | 7/2009 | Frandsen |
| 2009/0203602 A1 | 8/2009 | Gelber et al. |
| 2010/0086922 A1 | 4/2010 | Bryant |
| 2010/0323381 A1 | 12/2010 | Bergen, III et al. |
| 2011/0117021 A1 | 5/2011 | Smith et al. |
| 2011/0151494 A1 | 6/2011 | Koomen et al. |
| 2012/0315645 A1 | 12/2012 | Kaur et al. |
| 2012/0322073 A1 | 12/2012 | Lopez-Girona |
| 2013/0185096 A1 | 7/2013 | Giusti |
| 2014/0045276 A1 | 2/2014 | Singh et al. |
| 2014/0186332 A1 | 7/2014 | Ezrn et al. |
| 2014/0242072 A1 | 8/2014 | Hansson |
| 2014/0242624 A1 | 8/2014 | Valliere-Douglass |
| 2015/0204884 A1* | 7/2015 | Robblee ................ C07K 16/00 424/133.1 |
| 2015/0340219 A1 | 11/2015 | Mellors |
| 2016/0041184 A1 | 2/2016 | Barnidge et al. |
| 2016/0206660 A1 | 7/2016 | Shi et al. |
| 2016/0257763 A1 | 9/2016 | Von Kreudenstein et al. |
| 2017/0023584 A1 | 1/2017 | Murray et al. |
| 2018/0267057 A1 | 9/2018 | Barnidge et al. |
| 2019/0195888 A1 | 6/2019 | Barnidge et al. |

FOREIGN PATENT DOCUMENTS

| | | |
|---|---|---|
| WO | WO 2014/109927 | 7/2014 |
| WO | WO 2014/150170 | 9/2014 |
| WO | WO 2015/154052 | 10/2015 |
| WO | WO 2016/018978 | 2/2016 |
| WO | WO 2017/022315 | 2/2017 |

OTHER PUBLICATIONS

Abcam, "Understanding secondary antibodies" 2012, 12 pages, downloaded from http://docs.abcam.com/pdf/general/understanding_secondary_antibodies.pdf.

Abraham et al., "Characterization of free immunoglobulin light chains (LC) by mass spectrometry in light chain-associated (AL) amyloidosis," American Society of Hematology 43rd Annual Meeting, part 2, Orlando, Florida, USA, 98(11 Pt 2), p. 31b, Abstract#3722, Nov. 16, 2001.

Abraham et al., "Trimolecular complexes of lamda light chain dimers in serum of a patient with multiple myeloma," Clin Chem., 48(10):1805-1811, Oct. 2002.

Adamczyk et al., "Papain digestion of different mouse IgG subclasses as studied by electrospray mass spectrometry," J Immun Methods., 237:95-104, 2000.

Anonymous: "KappaSelect LambdaFabSelect," Data File 28-9448-22 AB, Mar. 1, 2012, Retrieved from the Internet: URL: https://www.gelifesciences.co.jp/catalog/pdf/Kappaselect_LamdaFabSelect.pdf Retrieved on Sep. 22, 2017, 4 pages.

Arun et al., "Immunohistochemical examination of light-chain expression (lambda/kappa ratio) in canine, feline, equine, bovine and porcine plasma cells," Zentralbl Veterinarmed A., 43(9):573-576, Nov. 1996.

Aucouturier et al., "Monoclonal immunogloblin light chains associated to Fanconi's syndrome," Monoclonal Gammopathies and the Kidney, 2003, 87-92.

Awad et al., "Analyses of cerebrospinal fluid in the diagnosis and monitoring of multiple sclerosis," J Neuroimmunol., 219(1-2):1-7, Epub Sep. 25, 2009.

Barnidge et al., "Monitoring free light chains in serum using mass spectrometry," Clinical Chemistry and Laboratory Medicine (CCLM). ISSN (Online) 1437-4331, ISSN (Print) 1434-6621, DOI: 10.1515/cclm-2015-0917, Feb. 2016.

Barnidge et al., "Monitoring M-proteins in patients with multiple myeloma using heavy-chain variable region clonotypic peptides and LC-MS/MS," J Proteome Res., 13(4):1905-1910, Epub Mar. 5, 2014.

Barnidge et al., "Phenotyping polyclonal kappa and lambda light chain molecular mass distributions in patient serum using mass spectrometry," J Proteome Res., 13(11):5198-5205, Epub Aug. 26, 2014.

Barnidge et al., "Using MALDI-TOF MS to Screen for Monoclonal Gammopathies in Serum and Urine," 61st Annual ASMS Conference on Mass Spectrometry and Allied Topics, Minneapolis, MN, Jun. 9-13, 2013, 1 page poster.

Barnidge et al., "Using mass spectrometry to monitor monoclonal immunoglobulins in patients with a monoclonal gammopathy," J Proteome Res., 13(3):1419-1427, Epub Feb. 11, 2014.

Barnidge, "Monitoring specific IgG tryptic peptides in multiple myeloma using the TripleTOF™ 5600 System," AB SCIEX Annual Users Meeting at ASMS, May 20, 2012, 28 slides.

Bennett et al., "Monitoring papain digestion of a monoclonal antibody by electrospray ionization mass spectrometry," Analytical Biochemistry., 245:17-27,1997.

Berg et al., "Mass spectrometry based proteomic analysis identifies two distinct types of cutaneous amyloidosis," Mod Pathol., vol. 22; p. 100A, 2009.

Bergen et al., "Characterization of amyloidogenic immunoglobulin light chains directly from serum by on-line immunoaffinity isolation," Biomedical Chromatography, 18(3):191-201, Apr. 1, 2004.

Bergon et al., "Linearity and detection limit in the measurement of serum M-protein with the capillary zone electrophoresis system Capillarys®," Clinical Chemistry and Laboratory Medicine, 43:721-723, 2005.

Bermudez-Crespo et al., "A better understanding of molecular mechanisms underlying human disease," Proteomics Clinical Applications, 1:983-1003, 2007.

Biosis accession No. PREV200200151435, 2 pages, Nov. 2001 Abstract only.

Biosis accession No. PREV201100424453, 2 pages, Nov. 2010 Abstract only.

Bois et al., "Cutaneous amyloidosis: mass spectrometry based proteomic analysis reveals diverse etiology associated with unique histopathological features," Mod Pathol., 26:320A-321A, Feb. 2013.

Boissinot et al., "Up-Regulation of Anti-Inflammatory, STAT3-Activating Hepatocyte Growth Factor and Interleukin-11 in Polycythemia Vera Is Independent of JAK2V617F and Contributes to the Growth of Clonal Erythroblasts," Blood, 116(21):796, Nov. 2010, 52nd Annual Meeting of the American Society of Hematology, Orlando, FL, USA Dec. 4-7, 2010.

Bourell et al., "Electrospray ionization mass spectrometry of recombinantly engineered antibody fragments," Anal Chem., 66:2088-2095, 1994.

Bradwell et al., "Highly sensitive, automated immunoassay for immunoglobulin free light chains in serum and urine," Clin Chem., 47(4):673-680, Apr. 2001.

Brochet et al., "IMGT/V-QUEST: the highly customized and integrated system for IG and TR standardized V-J and V-D-J sequence analysis," Nucleic Acids Res., 36(Web Server issue):W503-W508, Epub May 24, 2008.

Butler et al., "Immunoglobulins, antibody repertoire and B cell development," Dev Comp Immunol., 33(3):321-333, Epub Sep. 18, 2008.

Chen et al., "Characterization of protein therapeutics by mass spectrometry: recent developments and future directions," Drug Discovery Today., 16:58-64, 2011.

Cheung et al., "A proteomics approach for the identification and cloning of monoclonal antibodies from serum," Nature Biotechnology., 30:447-452, 2012.

Cohen., "Antibody structure," J Clin Path., 28 Suppl, 6:1-7, 1975.

Cordoba et al., "Non-enzymatic hinge region fragmentation of antibodies in solution," J Chromatography B., 818:115-121, 2005.

(56) References Cited

OTHER PUBLICATIONS

De Costa et al., "Sequencing and Quantifying IgG Fragments and Antigen-Binding Regions by Mass Spectrometry" Journal of Proteome Research, 9:2937-2945, Epub Apr. 14, 2010.

Dekker et al., "An Antibody-Based Biomarker Discovery Method by Mass Spectrometry Sequencing of Complementarity Determining Regions," Analytical and Bioanalytical Chemistry, 399:1081-1091, 2011.

Dogan et al., "Leukocyte Chemotactic Factor 2 Amyloidosis: A Novel Type of Amyloidosis That Mimics AL Amyloidosis," presented at The United States and Canadian Academy of Pathology Annual Meeting, Mar. 2009, 1 page.

Favereaux et al., "Serum IgG antibodies to P0 dimer and 35 kDa P0 related protein in neuropathy associated with monoclonal gammopathy," J Neurol Neurosurg Psychiatry., 74:1262-1266, 2003.

Fortini et al., "Cerebrospinal fluid oligoclonal bands in the diagnosis of multiple sclerosis. Isoelectric focusing with IgG immunoblotting compared with high-resolution agarose gel electrophoresis and cerebrospinal fluid IgG index," Am J Clin Pathol., 120(5):672-675, Nov. 2003.

Frangione, B., "Structure of Human Immunoglobulins and their Variants" B. Benacerraf (ed) Immunogenetics and Immunodeficiency, 1-53, 1975.

Gebski et al., "Affinity chromatography applications with single-domain antibodies," Bioprocess International., Aug. 1, 2013, Retrieved from the Internet: URL:http://www.bioprocessintl.com/2013/affinity-chromatography-applications-with-single-domain-antibodies-345480/ Retrieved on Sep. 22, 2017.

GenBank Accession AAA59107, "immunoglobulin lambda light chain C2 region, partial [Homo sapiens]," May 4, 2000, 2 pages.

Hagman et al., "Absolute quantification of monoclonal antibodies in biofluids by liquid chromatography-tandem mass spectrometry," Analytical Chemistry, 80(4):1290-1296, Feb. 15, 2008.

Hagmann et al., "Characterization of the F(ab')2 fragment of a murine monoclonal antibody using capillary isoelectric focusing and electrospray ionization mass spectrometry," J Chromatography A., 816:49-58, 1998.

Haraldsson et al., "Determination of kappa and lambda light chains in serum immunoglobulins G, A and M," Ann Clin Biochem., 28 (Pt 5):461-466, Sep. 1991.

Heudi et al., "Towards absolute quantification of therapeutic monoclonal antibody in serum by LC-MS/MS using isotope-labeled antibody standard and protein cleavage isotope dilution mass spectrometry," Anal Chem., 80(11):4200-4207, Epub May 9, 2008.

Hieter et al., "Clustered arrangement of immunoglobulin constant region genes in man," Nature, 294:536-540, 1981.

Hsieh et al., "Elucidation of potential bortezomib response markers in multiple myeloma patients," Journal of Pharmaceutical and Biomedical Analysis, 49:115-122, 2009.

Jagannath et al., "Value of serum free light chain testing for the diagnosis and monitoring of monoclonal gammopathies in hematology," Clin Lymphoma Myeloma, 7(8):518-523, Sep. 2007.

Jemal et al., "Cancer statistics, 2003," CA Cancer J Clin., 53(1):5-26, Jan.-Feb. 2003.

Jones et al., "A protocol for 'enhanced pepsin digestion': a step by step method for obtaining pure antibody fragments in high yield from serum," J of Immunol Methods., 275:239-250, 2003.

Joosten et al., "The production of antibody fragments and antibody fusion proteins by yeasts and filamentous fungi," Microbial Cell Factories., 2:1, 15 pages, 2003.

Kabat et al., "An electrophoretic study of the protein components in cerebrospinal fluid and their relationship to the serum proteins," J Clin Invest., 21(5):571-577, Sep. 1942.

Kaltashov et al., "Advances and challenges in analytical characterization of biotechnology products: Mass spectrometry-based approaches to study properties and behavior of protein therapeutics," Biotechnology Advances., 30:210-222, 2012.

Kaplan et al., "Free light chains in plasma of patients with light chain amyloidosis and non-amyloid light chain deposition disease. High proportion and heterogeneity of disulfide-linked monoclonal free light chains as pathogenic features of amyloid disease," British Journal of Haematology, 144:705-715, 2008.

Kohlhagen, "Using MALDI-TOF MS to Screen for Monoclonal Proteins in Serum," The Association for Mass Spectrometry Applications to the Clinical Lab [online] 2015. Retrieved from the Internet: <URL: https://www.msacl.org/2015_US_Long_Abstracts/201412041312_53747.pdf>, MSACL 2015 US: Preliminary Conference Program, San Diego, CA, Mar. 28-Apr. 1, 2015, 2 pages.

Koomen et al., "Proteomic contributions to personalized cancer care," Molecular & Cellular Proteomics, 7.10:1780-1794, 2008.

Kowarik et al., "The cerebrospinal fluid immunoglobulin transcriptome and proteome in neuromyelitis optica reveals central nervous system-specific B cell populations," J Neuroinflammation., 12:19, Jan. 28, 2015.

Kroon et al., "Identification of sites of degradation in a therapeutic monoclonal antibody by peptide mapping," Pharmaceutical Research., 9:1386-1393, 1992.

Landgren et al., "Monoclonal gammopathy of undetermined significance (MGUS) consistently precedes multiple myeloma: a prospective study" Blood, 113(22):5412-5417, May 28, 2009.

Lebeau et al., "Generalized crystal-storing histiocytosis associated with monoclonal gammopathy: molecular analysis of a disorder with rapid clinical course and review of the literature," Blood., 100:1817-1827, 2002.

Lefranc, "IMGT®, the International ImMunoGeneTics Information System®", Cold Spring Harb Protoc., 2011(6):595-603, Jun. 1, 2011.

Leung et al., "Monoclonal gammopathy of renal significance: when MGUS is no longer undetermined or insignificant," Blood, 120:4292-4295, 2012.

Li et al., "General LC-MS/MS method approach to quantify therapeutic monoclonal antibodies using a common whole antibody internal standard with application to preclinical studies," Analytical Chemistry, 84:1267-1273, 2012.

Li et al., "Simultaneous analysis of multiple monoclonal antibody biotherapeutics by LC-MS/MS method in rat plasma following cassette-dosing," AAPS J., 15(2):337-346, Epub Dec. 12, 2012.

Lindop et al., "Molecular signature of a public clonotypic autoantibody in primary Sjogren's syndrome: A "forbidden" clone in systemic autoimmunity," Arthritis & Rheumatism., 63(11):3477-3486, Oct. 28, 2011.

Liu et al., "Quantitation of a recombinant monoclonal antibody in monkey serum by liquid chromatography-mass spectrometry," Anal Biochem., 414(1):147-153, Epub Mar. 8, 2011.

Lu et al., "LC-MS Analysis of Polyclonal Human Anti-Neu5Gc Xeno-Autoantibodies Immunoglobulin G Subclass and Partial Sequence Using Multistep Intravenous Immunoglobulin Affinity Purification and Multienzymatic Digestion," Analytical Chemistry., 84(6):2761-2768, Mar. 20, 2012.

McBride et al., "Chromosomal location of human kappa and lambda immunoglobulin light chain constant region genes," J Exp Med., 155(5):1480-1490, May 1, 1982.

Merlini and Palladini, "Differential diagnosis of monoclonal gammopathy of undetermined significance" Hematology, 595-603, 2012.

Mukhopadhyay et al., "A tribute to Frank Anscombe and random central limit theorem from 1952," Sequential Analysis, 31(3):265-277, 2012.

Murphy et al., "Characterization of systemic amyloid deposits by mass spectrometry," Methods Enzymol., 412:48-62, 2006.

Nasr et al., "Immunotactoid glomerulopathy: clinicopathologic and proteomic study," Nephrol Dial Transplant., 27(11):4137-4146, Epub Aug. 7, 2012.

Obermeier et al., "Matching of oligoclonal immunoglobulin transcriptomes and proteomes of cerebrospinal fluid in multiple sclerosis," Nat Med., 14(6):688-693, Epub May 18, 2008.

Pang et al., "Biomarker discovery in urine by proteomics," Journal of Proteome Research, 1:161-169, Epub Feb. 16, 2002.

Radovic, V. V., "Recommendations for Use of Free Light Chain Assay in Monoclonal Gammopathies" Journal of Medical Biochemistry, 29:1-8, 2010.

Rajkumar et al., "Advances in the diagnosis, classification, risk stratification, and management of monoclonal gammopathy of undetermined significance: implications for recategorizing disease

(56) References Cited

OTHER PUBLICATIONS entities in the presence of evolving scientific evidence," *Mayo Clinic Proceedings.*, 85:945-948, 2010.
Remily-Wood et al., "A database of reaction monitoring mass spectrometry assays for elucidating therapeutic response in cancer," Proteomics Clinical Applications, 5:383-396, 2011.
Ren et al., "Reversed-phase liquid chromatography-mass spectrometry of site-specific chemical modifications in intact immunoglobulin molecules and their fragments," *J Chromatography A.*, 1179:198-204, 2008.
Rodriguez et al., "Immunoglobulin derived depositions in the nervous system: novel mass spectrometry application for protein characterization in formalin-fixed tissues," *Lab Invest.*, 88(10):1024-1037, Epub Aug. 18, 2008.
Sethi et al., "Mass spectrometry-based proteomic diagnosis of renal immunoglobulin heavy chain amyloidosis," *Clin J Am Soc Nephrol.*, 5:2180-2187, 2010.
Singh et al., "Cerebrospinal-fluid-derived immunoglobulin G of different multiple sclerosis patients shares mutated sequences in complementarity determining regions," *Mol Cell Proteomics*, 12(12):3924-3934, Epub Aug. 22, 2013.
Song et al., "Characterization of N-terminal processing of group VIA phospholipase A2 and of potential cleavage sites of amyloid precursor protein constructs by automated identification of signature peptides in LC/MS/MS analyses of proteolytic digests," *J Am Soc Mass Spectrom.*, 15(12):1780-1793, Dec. 2004.
Stubbs et al., "Anti-neurofilament antibodies in neuropathy with monoclonal gammopathy of undetermined significance produce experimental motor nerve conduction block," *Acta Neuropathology.*, 105:109-116, 2003.
Sun et al., "Immunoglobulin genes and diversity: what we have learned from domestic animals," *J Anim Sci Biotechnol.*, 3(1):18, Jun. 20, 2012.
Theis et al., "Immunoglobulin Light Chain Gene Constant Region Is an Invariable Part of Amyloid Deposits in AL Amyloidosis," *Blood*, 112(11):3128, Nov. 16, 2008.
Theis et al., "Mass spectrometry based proteomic analysis of AL amyloidosis: Immunoglobulin Light Chain Gene Constant Region is an Invariable Part of Amyloid Deposits and provides valuable diagnostic target," presented at The United States and Canadian Academy of Pathology Annual Meeting, Mar. 2009, 1 page.
Thermo Scientific, "Melon™ Gel IgG Spin Purification Kit" [online], 2011 [retrieved on Aug. 6, 2015]. Retrieved from the Internet: <URL: https://tools.lifetechnologies.com/content/sfs/manuals/MAN0011513_Melon_Gel_IgG_Spin_Purifi_UG.pdf>, 4 pages.
Thurgood et al., "An Immunodominant La/SSB autoantibody proteome derives from public clonotypes," *Clinical and Experimental Immunology.*, 174:237-244, Oct. 6, 2013.
VanDuijn et al., "Immune responses are characterized by specific shared immunoglobulin peptides that can be detected by proteomic techniques," Journal of Biological Chemistry, 285:29247-29253, Jul. 8, 2010.
Verheesen et al., "Beneficial properties of single-domain antibody fragments for application in immunoaffinity purification and immunoperfusion chromatography," *Biochim Biophys Acta.*, 1624(1-3):21-28, Dec. 5, 2003.
Vrana et al., "Amyloidosis typing based on Laser Microdissection and Mass Spectrometry of Paraffin-Embedded Tissue Biopsies" *Companion to Peripheral Neuropathy*, pp. 347-349, 2010.
Vrana et al., "Classification of Amyloidosis in Fat Aspiration Specimens Using Mass Spectrometry Based Proteomics," presented at the United States and Canadian Academy of Pathology Annual Meeting, Mar. 2009, 1 page.
Vrana et al., "Diagnosis and Classification of Amyloidosis in Abdominal Subcutaneous Fat Aspiration Specimens Using Mass Spectrometry Based Proteomics," *Blood*, 112(11):2710, Nov. 16, 2008.
Vrana et al., "Diagnosis and Typing of Cardiac Amyloidosis in Routine Clinical Specimens by Mass Spectrometry Based Proteomic Analysis," presented at The United States and Canadian Academy of Pathology Annual Meeting, Mar. 2009, 1 page.
Wang et al., "Construction of a Multiple Myeloma Diagnostic Model by Magnetic Bead-Based MALDI-TOF Mass Spectrometry of Serum and Pattern Recognition Software" Anatomical Record, 292:604-610, 2009.
Whiteaker et al., "Sequential multiplexed analyte quantification using peptide immunoaffinity enrichment coupled to mass spectrometry," *Mol Cell Proteomics.*, 11(6):10.1074/mcp.M111.015347, 2012,10 pages.
International Preliminary Report on Patentability for PCT/US2015/042580, dated Jan. 31, 2017, 10 pages.
International Search Report and Written Opinion for PCT/US2015/042580, dated Oct. 16, 2015, 16 pages.
Adamczyk et al., "Profiling of polyclonal antibody light chains by liquid chromatography/electrospray ionization mass spectrometry," Rapid Commun Mass Spectrom., 14:49-51, 2000.
Bondarenko et al., "Mass measurement and top-down HPLC/MS analysis of intact monoclonal antibodies on a hybrid linear quadrupole ion trap-orbitrap mass spectrometer," *J Am Soc Mass Spectrometry.*, 20:1415-1424, 2009.
Lu et al., "Detection of abundant proteins in multiple myeloma cells by proteomics," *J Proteomics Bioinform.*, 3(1):005-009, 2010.
Schaefer et al., "Residual serum monoclonal protein predicts progression-free survival in patients with previously untreated multiple myeloma," *Cancer.*, 116:640-646, 2010.
Zhang et al., "Characterization of variable regions of monoclonal antibodies by top-down mass spectrometry," *Anal Chem.*, 79:5723-5729, 2007.
Extended European Search Report in European Application No. 15827198.1, dated Nov. 23, 2017, 12 pages.
Ladwig et al., "Quantification of serum IgG subclasses by use of subclass-specific tryptic peptides and liquid chromatography-tandem mass spectrometry," *Clin Chem.*, 60(8):1080-1088, May 5, 2014.
Willrich et al., "Quantitation of infliximab using clonotypic peptides and selective reaction monitoring by LC-MS/MS," *International Immunopharmacology.*, 28(1): 513-520, Sep. 1, 2015.
Willrich et al., "Serum infliximab quantitation by LC-MS/MS in patients treated for inflammatory disorders," *Gastroenterology AGA Abstracts.*, Sal252, May 1, 2014, Retrieved from the internet: URL:https://ac.els-cdn.com/S0016508514608568/1-S2.0-S0016508514608568-mai n.pdf?_tid=e58e3b4c-caOa-lle7-96b2-OOOO0aabOf6b&acdnat=1510753563_74ab7a6bOb5f976b8c948a995d894fce, Retrieved on Nov. 15, 2017, Abstract Only.
Abraham et al., "Correlation of serum immunoglobulin free light chain quantification with urinary Bence Jones protein in light chain myeloma," Clin. Chem., 48(4):655-657, Apr. 2002.
Alldridge et al., "Proteome profiling of breast tumors by gel electrophoresis and nanoscale electrospray ionization mass spectrometry," J. Proteome. Res., 7(4):1458-1469, Apr. 2008.
Aucouturier et al., "Monoclonal Ig L chain and L chain V domain fragment crystallization in myeloma-associated Fanconi's syndrome" J. Immunol., 150(8 Pt 1):3561-3568, Apr. 1993.
Barratt et al., "Urine proteomics: the present and future of measuring urinary protein components in disease," CMAJ, 177(4):361-368, Aug. 2007.
Beck et al., "Characterization of therapeutic antibodies and related products," Anal. Chem., 85(2):715-736, Jan. 2013.
Breitkopf et al., "Detection of a rare BCR-ABL tyrosine kinase fusion protein in H929 multiple myeloma cells using immunoprecipitation (IP)-tandem mass spectrometry (MS/MS)," Proc. Natl. Acad. Sci. USA., 109(40):16190-16195, Oct. 2012.
Chung et al., "Thermodynamic stability of a kappal immunoglobulin light chain: relevance to multiple myeloma," Biophys. J., 88(6):4232-4242, Jun. 2005.
Coriu et al., "A molecular basis for nonsecretory myeloma," Blood, 104(3):829-831, Aug. 2004.
Dannoc et al., "High resolution proteome analysis of cryoglobulins using Fourier transform-ion cyclotron resonance mass spectrometry," Proteomics, 3(8):1425-1433, Aug. 2003.

(56) References Cited

OTHER PUBLICATIONS

Dear et al., "Acquired dysfibrinogenemia caused by monoclonal production of immunoglobulin lambda light chain," Haematologica., 92(11):e111-7, Nov. 2007.
Dillon et al., "Optimization of a reversed-phase high-performance liquid chromatography/mass spectrometry method for characterizing recombinant antibody heterogeneity and stability," J. Chromatogr. A., 1120(1-2):112-20, Jul. 2006.
Gucinski et al., "Evaluation of intact mass spectrometry for the quantitative analysis of protein therapeutics," Anal. Chem., 84(18):8045-8051, Sep. 2012.
Hill et al., "Serum free light chains: an alternative to the urine Bence Jones proteins screening test for monoclonal gammopathies," Clin. Chem., 52(9):1743-1748, Sep. 2006.
Holding et al., "Use of serum free light chain analysis and urine protein electrophoresis for detection of monoclonal gammopathies," Clin. Chem. Lab. Med., 49(1):83-88, Jan. 2011.
Johnson et al., "Cation exchange-HPLC and mass spectrometry reveal C-terminal amidation of an IgG1 heavy chain," Anal. Biochem., 360(1):75-83, Jan. 2007.
Kalaga et al., "Unexpected presence of polyreactive catalytic antibodies in IgG from unimmunized donors and decreased levels in rheumatoid arthritis," J. Immunol., 155(5):2695-2702, Sep. 1995.
Kaplan et al., "Immunoglobulin free light chain dimers in human diseases," The Scientific World Journal, 11:726-735, Mar. 2011.
Kaplan et al., "Isolation and biochemical characterization of plasma monoclonal free light chains in amyloidosis and multiple myeloma: a pilot study of intact and truncated forms of light chains and their charge properties," Clin. Chem. Lab. Med., 46(3):335-341, Mar. 2008.
Katzmann et al., "Serum reference intervals and diagnostic ranges for free kappa and free lambda immunoglobulin light chains: relative sensitivity for detection of monoclonal light chains," Clin. Chem., 48(9):1437-44, Sep. 2002.
Kyle et al., "Criteria for the classification of monoclonal gammopathies, multiple myeloma and related disorders: a report of the International Myeloma Working Group," Br. J. Haematol., 121(5):749-757, Jun. 2003.
Lavatelli et al., "A novel approach for the purification and proteomic analysis of pathogenic immunoglobulin free light chains from serum," Biochimica rt Biophysica Acta., 1814(3):409-419, Mar. 2011.
Marien et al., "Detection of monoclonal proteins in sera by capillary zone electrophoresis and free light chain measurements," Clin. Chem., 48(9):1600-1601, Sep. 2002.
Micallef, J. et al, Journal of Hennatology & Oncology 2010, 3, 11 pages.
Minnura et al., "Contrasting glycosylation profiles between Fab and Fc of a human IgG protein studied by electrospray ionization mass spectrometry," J. Immunol. Methods., 326(1-2):116-26, Sep. 2007.
Mohr et al., "High-efficiency nano- and micro-HPLC—high-resolution Orbitrap-MS platform for top-down proteomics," Proteomics., 10(20):3598-3609, Oct. 2010.
Murray et al., "Characterization of immunoglobulin by mass spectrometry with applications for the clinical laboratory," Crit. Rev. Clin Lab. Sci., 50(4-5):91-102, Jul.-Oct. 2013.
Piehler et al., "Quantitation of serum free light chains in combination with protein electrophoresis and clinical information for diagnosing multiple myeloma in a general hospital population," Clin. Chem., 54(11):1823-1830, Nov. 2008.
Rosati et al., "Exploring an orbitrap analyzer for the characterization of intact antibodies by native mass spectrometry," Angew. Chem. Int. Ed. Engl., 51(52):12992-12996, Dec. 2012.
Ruan et al., "Strategy and its implications of protein bioanalysis utilizing high-resolution mass spectrometric detection of intact protein," Anal. Chem., 83(23):8937-8944, Dec. 2011.
Wang et al., "Differentiation and quantification of endogenous and recombinant-methionyl human leptin in clinical plasma samples by immunocapture/mass spectrometry," J. Pharm. Biomed. Anal., 70:440-446, Nov. 2012.

Alge et al., "Proteomic Analysis of Plasma Exosome-Associated Proteins Reveals That Differences in Kappa: Lambda Ratios Predict Severe Acute Graft-Versus-Host Disease Early After Allogeneic Hematopoietic Stem Cell Transplantation," Blood., 1278, Nov. 2010.
Chiasserini et al., "CSF proteome analysis in multiple sclerosis patients by two-dimensional electrophoresis," Eur. J. Neurol., 15(9):998-1001, Sep. 2008.
D'Aguanno et al., "Differential cerebro spinal fluid proteome investigation of Leber hereditary optic neuropathy (LHON) and multiple sclerosis," 193(1-2):156-160, Dec. 2007.
Fan et al., "Identification of Niemann-Pick C1 disease biomarkers through sphingolipid profiling," J. Lipid. Res., 54(10):2800-2814, Oct. 2013.
Leung et al., "A novel and rapid approach to protein expression profiling of cerebrospinal fluid (CSF) from medulloblastoma patients using functionalized magnetic beads, AnchorChipTM technology, MALDI-TOf and MALDI-TOF/TOF mass spectrometry," 33rd Meeting of the Society of Neuroscience, 751.3, Nov. 2003.
Oeckl et al., "CSF concentrations of cAMP and cGMP are lower in patients with Creutzfeldt-Jakob disease but not Parkinson's disease and amyotrophic lateral sclerosis," PLoS One, 7(3):e32664, Mar. 2012.
Stoop et al., "Quantitative MALDI-FT-ICR analysis of cerebrospinal fluid of relapsing-remitting and primary progressive multiple sclerosis patients," Multiple Sclerosis., 15(9):583, Sep. 2009.
Zhaoyu et al., "Alteration of DBP levels in CSF of patients with MS by proteomics analysis," Cell Mol. Neurobiol., 29(2):203-210, Mar. 2009.
Barnidge and Murray, "Using Mass Spectrometry to Identify IgG Fc and Fab Fragments Produced by Plasmin in Patient Serum," Poster, Presented at American Society for Mass Spectrometry meeting on Jun. 7, 2016.
Bastian et al., "Intra- and interchain disulfide bridges of the human J chain in secretory immunoglobulin A," Biol. Chem. Hoppe Seyler., 373(12):1255-63, Dec. 1992.
Chevreux et al., "Fast analysis of recombinant monoclonal antibodies using IdeS proteolytic digestion and electrospray mass spectrometry," Analytical Biochemistry, 415(2):212-214, Aug. 2011.
De Lorenzi et al., "Urokinase links plasminogen activation and cell adhesion by cleavage of the RGD motif in vitronectin," EMBO reports, 17(7):982-98, Jul. 2016.
Drożdż Z et al., "Immunoglobulin cleavage by hypochlorous acid treatment," Clinica. Chimica. acta., 236(2):155-60, May 1995.
Faca et al., "Innovative proteomic approaches for cancer biomarker discovery," Biotechniques, 43(3):279-283, Sep. 2007.
Gadgil et al., "The LC/MS analysis of glycation of IgG molecules in sucrose containing formulations," Journal of Pharmaceutical Sciences, 96(10):2607-2621, Oct. 2007.
Hanash et al., "Mining the plasma proteome for cancer biomarkers," Nature, 452(7187):571-579, Apr. 2008.
Huse et al., "Purification of antibodies by affinity chromatography," Journal of biochemical and biophysical methods, 51(3):217-31, May 2002.
Kleennann et al., "Characterization of IgG1 immunoglobulins and peptide-Fc fusion proteins by limited proteolysis in conjunction with LC-MS," Analytical Chemistry, 80(6):2001-2009, Mar. 2008.
Kragten et al., "Site-specific analysis of the N-glycans on murine polymeric immunoglobulin A using liquid chromatography/electrospray mass spectrometry," Journal of Mass Spectrometry, 30(12):1679-86, Dec. 1995.
Legros et al., "Characterization of an anti-Borrelia burgdorferi OspA conformational epitope by limited proteolysis of monoclonal antibody-bound antigen and mass spectrometric peptide mapping," Protein Science, 9(5):1002-10, May 2000.
Mazur et al., "A platform for characterizing therapeutic monoclonal antibody breakdown products by 2D chromatography and top-down mass spectrometry," The AAPS journal, 14(3):530-41, Sep. 2012.
Mills et al., "Using mass spectrometry to quantify rituximab and perform individualized immunoglobulin phenotyping in ANCA-associated vasculitis," Analytical chemistry, 88(12):6317-25, Jun. 2016.

(56) References Cited

OTHER PUBLICATIONS

Qin et al., "Development of a "reverse capture" autoantibody microarray for studies of antigen-autoantibody profiling," Proteomics., 6(10):3199-209, May 2006.

Reid et al., "Rapid whole monoclonal antibody analysis by mass spectrometry: An ultra scale-down study of the effect of harvesting by centrifugation on the post-translational modification profile," Biotechnology and Bioengineering, 107(1):8595, Sep. 2010.

Sun et al., "Preparation and mass spectrometric study of egg yolk antibody (IgY) against rabies virus," Rapid communications in mass spectrometry, 15(9):708-12, May 2001.

Vrana et al., "Classification of amyloidosis by laser microdissection and mass spectrometry-based proteomic analysis in clinical biopsy specimens," Blood, 114(24):4957-4960, Dec. 2009.

Wagner-Rousset et al., "The way forward, enhanced characterization of therapeutic antibody glycosylation: comparison of three level mass spectrometry-based strategies," Journal of Chromatography B, 872(1-2):23-37, Sep. 2008.

Wang et al., "Molecular basis of assembly and activation of complement component C1 in complex with immunoglobulin G1 and antigen," Molecular cell, 63(1):135-45, Jul. 2016.

Yamazaki et al., "A proteolytic modification of AIM promotes its renal excretion," Scientific Reports, 6:38762, Dec. 2016.

\* cited by examiner

QUANTIFYING MONOCLONAL ANTIBODY THERAPEUTICS BY LC-MS/MS

CROSS REFERENCE TO RELATED APPLICATIONS

This application is a National Stage application under 35 U.S.C. § 371 of International Application No. PCT/US2015/042580, having an International Filing Date of Jul. 29, 2015, which claims the benefit of U.S. Provisional Ser. No. 62/030,493, filed Jul. 29, 2014. This disclosure of the prior applications is considered part of (and is incorporated by reference in) the disclosure of this application.

TECHNICAL FIELD

This disclosure relates to methods for quantifying monoclonal antibody therapeutics using mass spectrometry techniques.

BACKGROUND

Human monoclonal antibodies contain two identical heavy chain polypeptides (each about 54 kilodaltons in MW) and two identical light chain polypeptides (each about 24 kilodaltons in molecular weight) which are bound together by disulfide bonds. Each light chain and each heavy chain include a constant region and a variable region. The variable region is located on the N-terminal portion of each chain and the constant region is located on the C-terminal portion of each chain. The constant regions of the light chains and heavy chains have different amino acid sequences, and can be used to identify the isotype of the heavy or light chain. In humans, there are two different isotypes of light chain polypeptides referred to as either kappa or lambda; and five different isotypes of heavy chain polypeptides referred to as gamma (IgG), alpha (IgA), mu (IgM), epsilon (IgE), and delta (IgD).

Clinical laboratories currently monitor and quantify the levels of monoclonal antibody therapeutics in patients receiving such treatment using immunoassays, such as ELISA.

SUMMARY

Provided herein is a method for quantifying a monoclonal antibody therapeutic in a sample, comprising: providing a sample comprising a monoclonal antibody therapeutic; adding an internal standard to the sample, wherein the internal standard is a non-isotopically labeled immunoglobulin from a non-human species; and subjecting the sample to a mass spectrometry technique to quantify the monoclonal antibody therapeutic in the sample.

In some embodiments, the monoclonal antibody therapeutic is a humanized monoclonal antibody therapeutic. In some embodiments, the monoclonal antibody therapeutic is a human monoclonal antibody therapeutic. In some embodiments, the monoclonal antibody therapeutic is selected from the group consisting of: infliximab, alemtuzumab, eculizumab, rituximab and adalimumab. For example, the monoclonal antibody therapeutic can be infliximab.

In some embodiments, the non-isotopically labeled immunoglobulin from a non-human species is a non-human IgG antibody. In some embodiments, the non-isotopically labeled immunoglobulin from a non-human species is a horse IgG.

In some embodiments, the method further comprises digesting the antibodies in the sample prior to the mass spectrometry step. In some embodiments, digesting the antibodies comprises digestion using trypsin.

In some embodiments, the method further comprises purifying the sample prior to the mass spectrometry step. For example, the sample may be purified using antibody affinity resin purification.

In some embodiments, the mass spectrometry technique comprises a tandem mass spectrometry (MS/MS) technique. In some embodiments, the mass spectrometry technique comprises an LC-MS/MS technique. For example, the mass spectrometry technique can be a LC-ESI TRIPLE QUAD MS. In some embodiments, the mass spectrometry technique comprises the use of positive ion mode. In some embodiments, the mass spectrometry technique comprises selective reaction monitoring (SRM) analysis. In some embodiments, the SRM analysis comprises monitoring the horse IgG constant region.

In some embodiments, the monoclonal antibody therapeutic light chains are decoupled from the monoclonal antibody therapeutic heavy chains prior to the mass spectrometry step.

In some embodiments, quantifying the monoclonal antibody therapeutic in the sample comprises measuring the variable region peptide of the monoclonal antibody therapeutic. In some embodiments, quantifying the monoclonal antibody therapeutic in the sample comprises subjecting the sample to a LC-MS/MS mass spectrometry technique.

In some embodiments, the sample is a biological sample. In some embodiments, the biological sample is a whole blood sample, serum sample, saliva sample, plasma sample, or urine sample. For example, the biological sample can be a serum sample.

Also provided herein is a method of monitoring a treatment of a disorder in a subject, wherein the disorder is treated with a monoclonal antibody therapeutic, comprising:
  a) providing a first sample of the subject during treatment;
  b) providing a second sample of the subject on a subsequent treatment or after treatment;
  c) subjecting the first and second sample to a mass spectrometry technique comprising an internal standard to obtain a mass spectrum of the sample, wherein the internal standard is a horse IgG;
  d) quantifying the monoclonal antibody therapeutic in the first and second sample; and
  e) comparing the amounts from the first and second sample.

In some embodiments, the monitoring a treatment of a disorder in a subject comprises quantifying a monoclonal antibody therapeutic in a sample.

In some embodiments, the disorder is one that is treated with a humanized monoclonal antibody therapeutic. In some embodiments, the disorder is one that is treated with a human monoclonal antibody therapeutic. In some embodiments, the disorder is one that is treated with infliximab, alemtuzumab, eculizumab, rituxumab or adalimumab. For example, the disorder can be one that is treated with infliximab.

Unless otherwise defined, all technical and scientific terms used herein have the same meaning as commonly understood by one of ordinary skill in the art to which this description belongs. Methods and materials are described herein for use in the present invention; other, suitable methods and materials known in the art can also be used. The materials, methods, and examples are illustrative only and not intended to be limiting. All publications, patent applications, patents, and other references mentioned herein are incorporated by reference in their entirety. In case of conflict, the present specification, including definitions, will control. Other features and advantages of the invention will be apparent from the following detailed description and figures, and from the claims.

DETAILED DESCRIPTION

Monoclonal antibody therapeutics is a rapidly growing class of drugs. This class of protein drug presents unique challenges when compared to small molecule drugs for quantitating levels in patients. Since the monoclonal antibody therapeutics have very similar molecular structure to normal background polyclonal antibodies in patients sera, most methods used for quantifying them rely on the interaction of the monoclonal antibody with its target antigen. Such methods, while useful, can be subject to cross reactivity with other antibodies present in the sera. This method directly quantitates the monoclonal antibody without the need for interaction with the antigen. Provided herein are methods of quantifying monoclonal antibody therapeutics that include monitoring tryptic peptides from the unique variable regions of the monoclonal antibody and comparing them to the constant regions of a non-human antibody added as an internal standard. This method offers advantages compared to other methods as the addition of the non-human antibody as internal standard affords enhanced accuracy. For example, not only does the standard have a similar, yet distinct, mass profile, but it is also similarly reactive through all preparatory steps including, for example, enzymatic digestion and purification.

Figure 1:
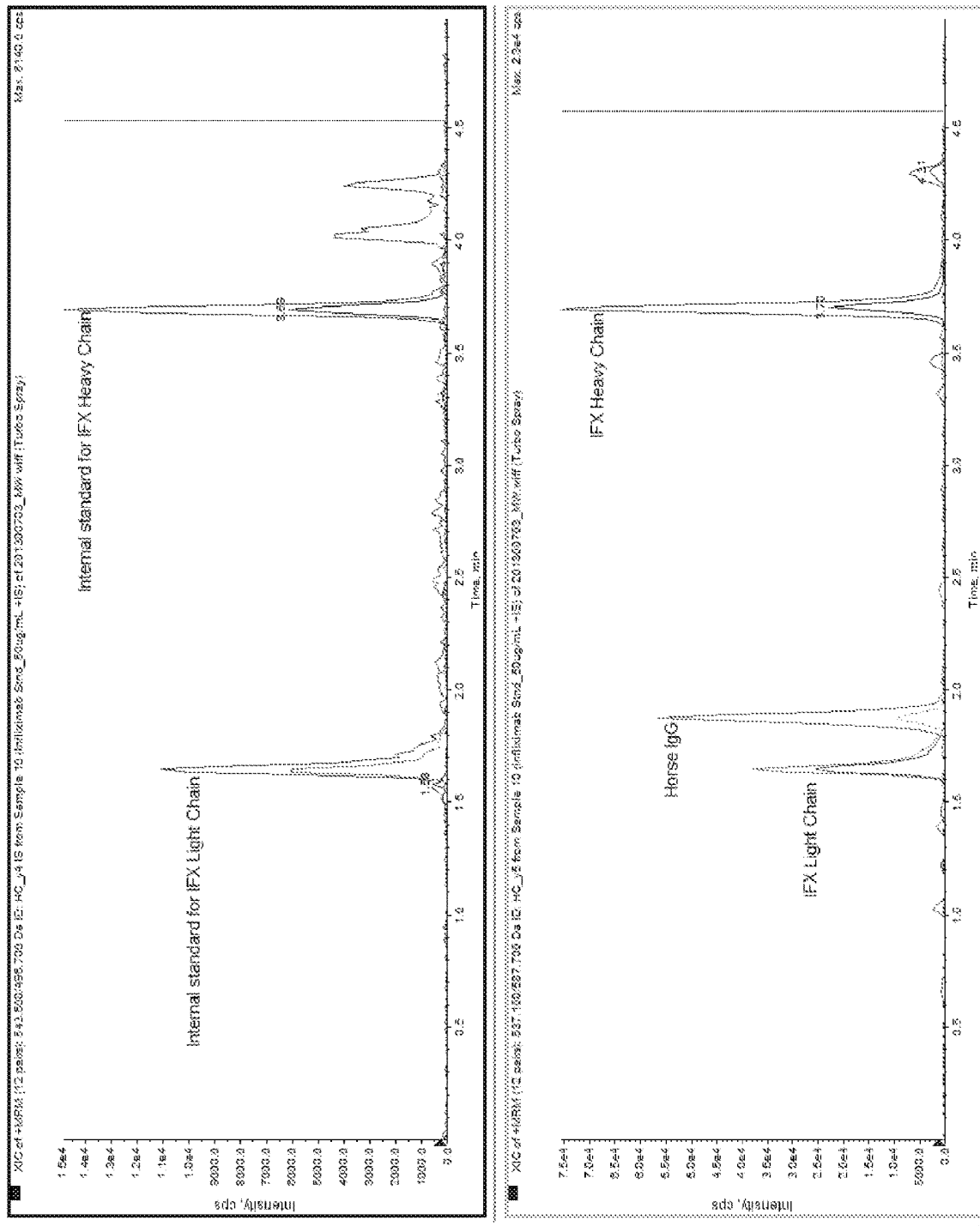
FIG. 1 provides liquid chromatograms with peaks for heavy and light chain labeled infliximab internal standard (top graph), and with horse IgG and infliximab heavy and light chain transitions (bottom graph).

FIG. 1 presents an example of how in silico prediction of peptide digestion patterns on a monoclonal antibody therapeutic would be correlated with an LC-MS/MS chromatogram. A sample containing an antibody therapeutic would first be processed, for example, by enzymatic digestion, and then analyzed by mass spectrometry, for example, using LC-MS/MS. The most abundant peptides unique to the heavy and light chain variable regions of the monoclonal antibody therapeutic would be chosen for monitoring. The expected LC pattern in an LC-MS/MS would exhibit two peaks correlating to the peptides from the heavy and light chains of the monoclonal antibody therapeutic (top graph). Known amounts of a non-human monoclonal antibody, for example, horse IgG, can also be added as an internal standard to samples containing the human monoclonal antibody therapeutic. The intact horse immunoglobulin represents an improvement over commonly used isotopically labeled peptides since it is present in the purification and digestion step and normalizes for sample to sample differences in sample preparation. Quantitation of the monoclonal antibody therapeutic may be accomplished using standard SRM analysis to generate a standard curve, for example, FIG. 2, to be used to calculate concentrations in biological samples containing unknown amounts of the monoclonal antibody therapeutic.

Provided herein is a method for quantifying a monoclonal antibody therapeutic in a sample, comprising: providing a sample comprising a monoclonal antibody therapeutic; adding an internal standard to the sample, wherein the internal standard is a non-isotopically labeled immunoglobulin from a non-human species; and subjecting the sample to a mass spectrometry technique to quantify the monoclonal antibody therapeutic in the sample.

In some embodiments, the monoclonal antibody therapeutic is a humanized monoclonal antibody therapeutic. In some embodiments, the monoclonal antibody therapeutic is a human monoclonal antibody therapeutic. In some embodiments, the monoclonal antibody therapeutic is selected from the group consisting of: infliximab, alemtuzumab, eculizumab, rituximab, adalimumab, and mixtures thereof. For example, the monoclonal antibody therapeutic can be infliximab.

In some embodiments, the non-isotopically labeled immunoglobulin from a non-human species is a non-human IgG antibody. In some embodiments, the non-isotopically labeled immunoglobulin from a non-human species is a horse IgG. In some embodiments, the non-isotopically labeled immunoglobulin from a non-human species is a mouse IgG.

In some embodiments, the immunoglobulins are purified from the sample before digestion using precipitation, protein A/G affinity chromatography, affinity resin purification, chemical fractionation (e.g., antibody purification kits, such as Melon Gel Purification). For example, the sample may be purified using affinity resin purification.

In some embodiments, the method further comprises digesting one or more antibodies (e.g., the monoclonal antibody therapeutic and the internal standard) in the sample prior to the mass spectrometry step. In some embodiments, digesting the antibodies comprises digestion using trypsin.

In some embodiments, the method further comprises purifying the sample prior to the mass spectrometry step. In some embodiments, the sample may be purified via centrifugation, filtration, ultrafiltration, dialysis, ion exchange chromatography, size exclusion chromatography, gel electrophoresis, or capillary electrophoresis.

In some embodiments, the mass spectrometry technique comprises a tandem mass spectrometry (MS/MS) technique. In some embodiments, the mass spectrometry technique comprises an LC-MS/MS technique. For example, the mass spectrometry technique can be LC-ESI TRIPLE QUAD MS. In some embodiments, the mass spectrometry technique comprises the use of positive ion mode. In some embodiments, the mass spectrometry technique comprises selective reaction monitoring (SRM) analysis. In some embodiments, the SRM analysis comprises monitoring the horse IgG constant region.

In some embodiments, the monoclonal antibody therapeutic light chains are decoupled from the monoclonal antibody therapeutic heavy chains prior to the mass spectrometry step.

In some embodiments, quantifying the monoclonal antibody therapeutic in the sample comprises measuring the variable region peptide of the monoclonal antibody therapeutic. In some embodiments, quantifying the monoclonal antibody therapeutic in the sample comprises subjecting the sample to a LC-MS/MS mass spectrometry technique.

In some embodiments, the sample is a biological sample. In some embodiments, the biological sample is a whole blood sample, serum sample, saliva sample, plasma sample, or urine sample. For example, the biological sample can be a serum sample.

Also provided herein is a method of monitoring a treatment of a disorder in a subject, wherein the disorder is treated with a monoclonal antibody therapeutic, comprising:
a) providing a first sample of the subject during treatment;
b) providing a second sample of the subject on a subsequent treatment or after treatment;
c) subjecting the first and second sample to a mass spectrometry technique comprising an internal standard to obtain a mass spectrum of the sample, wherein the internal standard is a horse IgG;
d) quantifying the monoclonal antibody therapeutic in the first and second sample; and
e) comparing the amounts from the first and second sample.

In some embodiments, the monitoring a treatment of a disorder in a subject comprises quantifying a monoclonal antibody therapeutic in a sample.

In some embodiments, the disorder is one that is treated with a humanized monoclonal antibody therapeutic. In some embodiments, the disorder is one that is treated with a human monoclonal antibody therapeutic. In some embodiments, the disorder is one that is treated with infliximab, alemtuzumab, eculizumab, rituximab, adalimumab, or a combination thereof. For example, the disorder can be one that is treated with infliximab.

Samples and Sample Preparation

A sample for analysis can be any biological sample, such as a tissue (e.g., adipose, liver, kidney, heart, muscle, bone, or skin tissue) or biological fluid (e.g., blood, serum, plasma, urine, lachrymal fluid, or saliva) sample. The biological sample can be from a subject that has been treated with a human monoclonal antibody, which includes, but is not limited to, a mammal, e.g. a human, dog, cat, primate, rodent, pig, sheep, cow, and horse. In some embodiments the biological sample comprises an exogenous monoclonal antibody. A sample can also be a man-made reagent, such as a mixture of known composition or a control sample.

A sample can be treated to remove components that could interfere with the mass spectrometry technique. A variety of techniques known to those having skill in the art can be used based on the sample type. Solid and/or tissue samples can be ground and extracted to free the analytes of interest from interfering components. In such cases, a sample can be centrifuged, filtered, and/or subjected to chromatographic techniques to remove interfering components (e.g., cells or tissue fragments). In yet other cases, reagents known to precipitate or bind the interfering components can be added. For example, whole blood samples can be treated using conventional clotting techniques to remove red and white blood cells and platelets.

Monoclonal antibodies can be isolated from the samples or enriched (i.e. concentrated) in a sample using standard methods known in the art. Such methods include removing one or more non-monoclonal antibody contaminants from a sample. In some embodiments, the samples can be enriched or purified using centrifugation, filtration, ultrafiltration, dialysis, ion exchange chromatography, size exclusion chromatography, protein A/G affinity chromatography, affinity purification, precipitation, gel electrophoresis, capillary electrophoresis, and chemical fractionation (e.g., antibody purification kits, such as Melon Gel Purification). For example, the monoclonal antibodies can be purified by chemical-based fractionation, e.g., Melon Gel Chromatography (Thermo Scientific), where Melon Gel resins bind to non-monoclonal antibody proteins in a sample and allow monoclonal antibodies to be collected in the flow-through fraction; or by affinity purification, e.g., by Protein A, Protein G, or Protein L purification, where monoclonal antibodies are bound by those proteins at physiologic pH and then released from the proteins by lowering the pH. When serum, plasma, or whole blood samples are used, a sample, such as a 10-250 µl sample, e.g., a 50 µl, can be directly subjected to Melon Gel, Protein A, Protein G, or Protein L purification. Size exclusion principles such as a TurboFlow column can also be employed to separate the non-monoclonal antibody contaminants from a sample. When urine samples are used, a urine sample can be buffered, e.g., a 50 µl urine sample can be diluted first with 50 µl of 50 mM ammonium bicarbonate.

In some embodiments, the monoclonal antibodies, or the heavy and/or light chains thereof, are substantially isolated. By "substantially isolated" is meant that the monoclonal antibodies are at least partially or substantially separated from the sample from which they were provided. Partial separation can include, for example, a sample enriched in the monoclonal antibodies (i.e., the heavy and/or light chains). Substantial separation can include samples containing at least about 10%, at least about 20%, at least about 30%, at least about 40%, at least about 50%, at least about 60%, at least about 70%, at least about 80%, at least about 90%, at least about 95%, at least about 97%, or at least about 99% by weight of the monoclonal antibody, or the heavy and/or light chains thereof. Methods for isolating monoclonal antibodies, such as those described above, are routine in the art.

Intact monoclonal antibodies can be further processed to decouple the light chains in a total monoclonal antibody sample from the heavy chains. Decoupling can be achieved by treating the total monoclonal antibodies with a reducing agent, such as DTT (2,3 dihydroxybutane-1,4-dithiol), DTE (2,3 dihydroxybutane-1,4-dithiol), thioglycolate, cysteine, sulfites, bisulfites, sulfides, bisulfides, TCEP (tris(2-carboxyethyl)phosphine), 2-mercaptoethanol, and salt forms thereof. In some embodiments, the reducing step is performed at elevated temperature, e.g., in a range from about 30° C. to about 65° C., such as about 55° C., in order to denature the proteins. In some embodiments, the sample is further treated, e.g., by modifying the pH of the sample or buffering the sample. In some embodiments, the sample can be acidified. In some embodiments, the sample can be neutralized (e.g., by the addition of a base such as bicarbonate).

Mass Spectrometry Methods

After sample preparation, a monoclonal antibody sample, such as a trypsin digested immunoglobulin enriched serum, can be subjected to a mass spectrometry (MS) technique, either directly or after separation on a high performance liquid chromatography column (HPLC). LC-MS/MS is an analytical technique that combines the physical separation capabilities of liquid chromatography with the mass analysis capabilities of mass spectrometry, and is suitable for detection and potential identification of chemicals in a complex mixture. Any LC-MS instrument can be used, e.g., the ABSciex 5000 Mass Spectrometer (AB SCIEX, Framingham, Mass., USA). In some embodiments, a reversed-phase C18 liquid chromatography HPLC column can be utilized. Any suitable reversed-phase C18 liquid chromatography HPLC column can be used, e.g., the Atlantis T3 3×100 mm. The ion mass spectrum can be analyzed for one or more peaks corresponding to one or more heavy or light chain peptides in the sample. In some embodiments, the ratio is determined by the peak area of the selected ion peak(s).

In some embodiments, electrospray ionization coupled to a quadrupole mass spectrometry (ESI Triple Quad MS) can be used to analyze the mass spectrum of a monoclonal antibody sample. A quadrupole mass analyzer (Q) consists of four cylindrical rods, set parallel to each other. In a quadrupole mass spectrometer, the quadrupole is the component of the instrument responsible for filtering sample ions based on their mass-to-charge ratio (m/z). Any ESI Triple Quad mass spectrometer can be used, e.g., the ABSciex API 5000 mass spectrometer.

Methods for Screening Biological Samples and for Diagnosing and Monitoring Disorders The mass spectrometry based methods provided herein can also be used for monitoring the treatment of a disorder in a subject. The disorder may be a disorder that is treated with a monoclonal antibody therapeutic. In such cases, the methods provided herein may be used to monitor the levels of monoclonal antibody therapeutic present in the subject during or after a treatment regimen. For example, in a treatment regimen that involves repeated monthly dosing of a monoclonal antibody therapeutic, the method may be used to quantitate the monoclonal antibody therapeutic at trough level prior to the subsequent dose. In some embodiments, information on the trough level may be used to determine whether the desired concentration for therapeutic treatment of the disorder is being reached, or whether the frequency or dosage of the therapy needs to be adjusted.

In some embodiments, the method provided herein may monitor a disorder selected from rheumatoid arthritis, psoriatic arthritis, ankylosing spondylitis, Crohn's disease (including adult and pediatric Crohn's disease), plaque psoriasis, ulcerative colitis (including adult and pediatric ulcerative colitis), B-cell chronic lymphocytic leukemia, paroxysmal nocturnal hemoglobinuria (PNH), atypical hemolytic uremic syndrome (aHUS), granulomatosis with polyangiitis (Wegener's granulomatosis), microscopic polyangiitis (MPA), CD-20 positive chronic lymphocytic leukemia, and non-Hodgkin lymphoma (including large B-cell and low-grade or follicular non-Hodgkin lymphoma). For example, the disorder can be rheumatoid arthritis.

In some embodiments, the monoclonal antibody therapeutic is a human monoclonal antibody therapeutic. In some embodiments, the monoclonal antibody therapeutic is selected from infliximab, alemtuzumab, eculizumab, rituximab, adalimumab, or any combination thereof. For example, the monoclonal antibody therapeutic can be infliximab.

EXAMPLES

General Methods.

Serum and Monoclonal Antibody Reagents:

Serum was collected from waste samples obtained from the clinical laboratory.

Reagents:

Ammonium bicarbonate, dithiothreitol (DTT), and formic acid were purchased from Sigma-Aldrich (St. Louis, Mo.). Melon Gel was purchased from Thermo-Fisher Scientific (Waltham Mass.). Water, acetonitrile, and 2-propanol were purchased from Honeywell Burdick and Jackson (Muskegon, Mich.).

Serum:

A volume of 50 µL of serum was enriched for monoclonal antibodies using Melon Gel following the manufacturer's instructions. After monoclonal antibody enrichment, 25 µL of sample was reduced by adding 25 µL of 100 mM DTT and 25 µL of 50 mM ammonium bicarbonate then incubated at 55° C. for 15 minutes before injection. Samples were placed into 96 deep-well PCR plates (300 µL volume) at 9° C. while waiting for injection.

Esi-Q-Tof Ms:

Spectra were collected on an ABSciex Triple Quad 5000 mass spectrometer (ABSciex, Vaughan ON, CA) in ESI positive mode with a Turbo V dual ion source with an automated calibrant delivery system (CDS). Source conditions were: IS: 5500, Temp: 500, CUR: 45, GS1: 35, GS2: 30, CE: 50±5. TOF MS scans were acquired from m/z 600-2500 with an acquisition time of 100 ms. Fragment ion scans were acquired from m/z 350-2000 with an acquisition time of 100 ms. The instrument was calibrated every 5 injections through the CDS using calibration solution supplied by the manufacturer.

MS Data Analysis:

Analyst TF v1.6 was used for instrument control. Data were viewed using Analyst TF v1.6 and PeakView v1.2.0.3. Peptides were separated on reverse-phase C18 liquid chromatography (Atlantis T3 3×100 mm) and subjected to MS/MS using an ABSciex 5000 triple quad MS instrument.

Example 1—Infliximab

Preparation of Sample

A list of tryptic peptides unique to the heavy and light chain variable regions were predicted by in silico digestion of infliximab variable region sequences found in the IMGT database (http://www.imgt.org/3Dstructure-DB). Infliximab (Remicade™, Janssen Biotech, Inc.) was reconstituted to 10 mg/mL in 50 mM ammonium bicarbonate, reduced, alkylated and digested with trypsin (1:20 enzyme:substrate ratio) at 37° C. for 4 hours. Digests were analyzed by IDA LC-ESI TRIPLE QUADMS. The most abundant peptides matching the in silico list were chosen for subsequent studies.

Quantitation of infliximab was accomplished using standard SRM analysis on an ABSciex API 5000 using pooled human serum from healthy controls or 50 mM ammonium bicarbonate, each spiked with infliximab. A 9-point standard curve was generated [blank, 0.25, 0.5, 1, 2, 5, 10, 20 and 50 µg/mL].

A known concentration of purified horse IgG (200 ug/mL) with a unique non-human constant region peptide was added to each sample as a pre-analytical digestion control along with stable isotope-labeled peptide internal standards to monitor HPLC retention times.

LC-MS/MS Analysis

Samples were processed to remove non-immunoglobulin proteins using the Melon Gel purification kit (Pierce, Rockford, Ill.), followed by trypsin digestion. Peptides were separated on reverse-phase C18 liquid chromatography (Atlantis T3 3×100 mm) and subjected to MS/MS. A typical chromatogram for the SRM analysis monitoring for the peptides for horse IgG constant region, and the heavy chain and light chain peptide from infliximab are shown in FIG. 1. FIG. 1 shows liquid chromatograms with peaks for heavy and light chain labeled infliximab internal standard (top graph), and with horse IgG and infliximab heavy and light chain transitions (bottom graph).

Correlation of Experimental Data to Expected Theoretical Results

Figure 2:
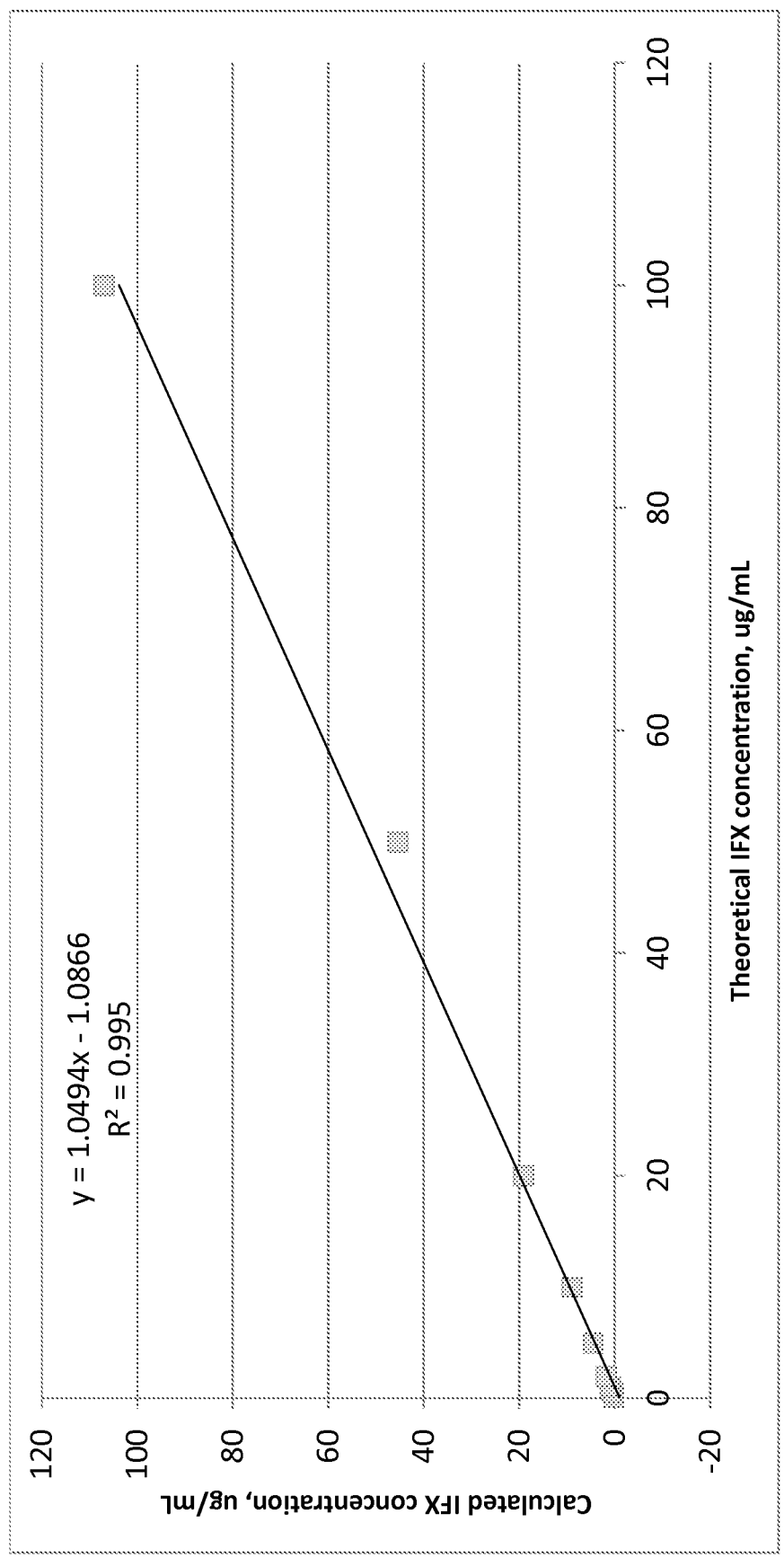
FIG. 2 shows a standard curve of infliximab in commercial pooled serum using heavy chain transition HCy4.

The ability to accurately quantitate the level of infliximab in patient sera was demonstrated by spiking known amounts of infliximab into patient serum and plotting the heavy chain peptide response as a function of drug level. The results of the normal pooled serum spiked at various levels of infliximab demonstrate that the peak areas are linearly correlated with infliximab levels (FIG. 2). FIG. 2 shows the measured and calculated infliximab concentration (y-axis; μg/mL) in comparison to the theoretical infliximab concentration (x-axis; μg/mL). The standard curve was generated with infliximab at 0 to 100 μg/mL concentrations in commercial pooled human serum using heavy chain transition HCy4.

Correlation of LC-MS/MS Concentrations to Other Methods

Figure 3:
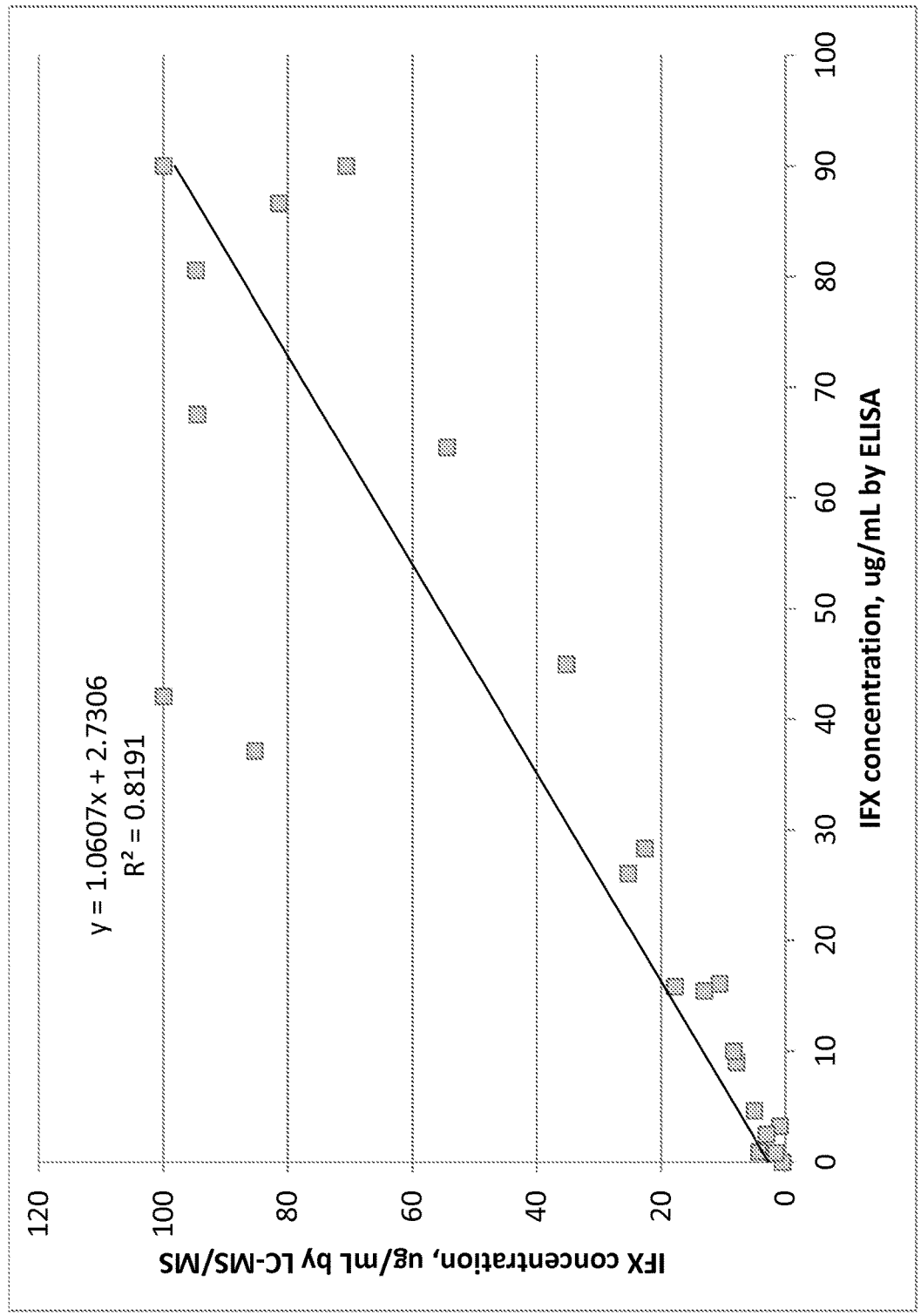
FIG. 3 shows a comparison of infliximab concentrations calculated using LC-MS/MS and those obtained from an ELISA method.

The LC-MS/MS method was applied to a series of patients who received infliximab treatments. The method was compared to a commercially available ELISA kit for infliximab (Immunodiagnostik, Germany). The resulting concentration versus time curves demonstrate the ability of the method to quantitate over time (FIG. 3). FIG. 3 shows the infliximab concentration as measured by the LC-MS/MS method (y-axis; μg/mL) as compared with that measured using the ELISA method (x-axis; μg/mL). The results demonstrate the LC-MS/MC method correlates to the ELISA method with a linear regression of $R^2=0.82$.

Example 2—Infliximab in Patients

The protocol was as performed in Example 1. Patients' immunoglobulins were purified by precipitation with 55 μL of a saturated ammonium sulfate solution prior to digestion and analysis.

Figure 4:
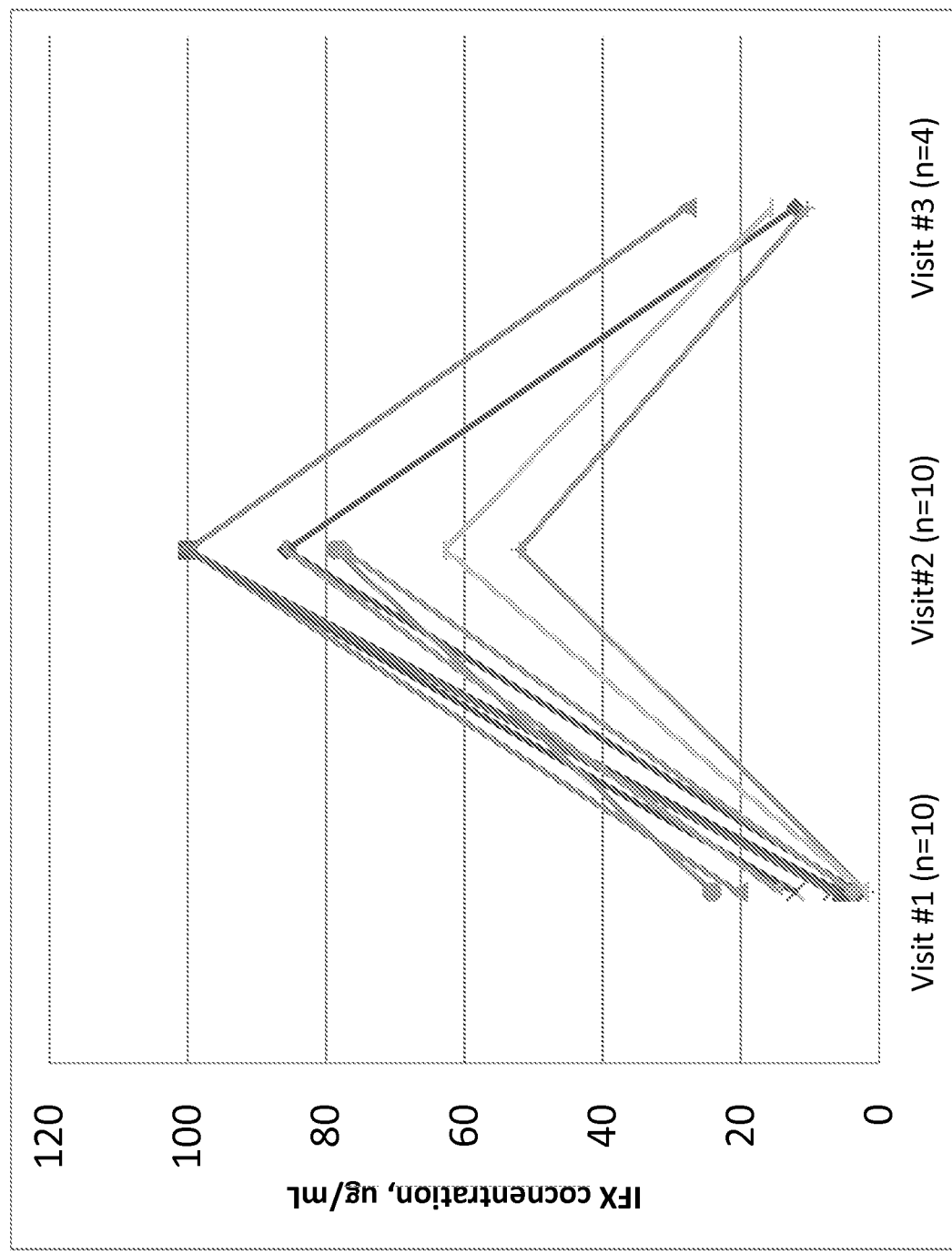
FIG. 4 provides results for infliximab levels measured by SRM LC-MS/MS in patients receiving infliximab infusions. Visit #1 was measured at trough levels; visit #2 at 48-72 hours after infliximab infusion; visit #3 at 28-32 days after infliximab infusion.

The LC-MS/MS method was used to monitor consenting patients who were receiving infliximab therapy. The results confirmed that this method may be useful to monitor concentrations of infliximab in patients. FIG. 4 shows the change in infliximab concentration (y-axis; μg/mL) over a series of three patient visits (x-axis) at trough level (visit #1), at 48-72 hours after infliximab infusion (visit #2), and at 28-32 days after infusion (visit #3).

Example 3—Alemtuzumab

A list of tryptic peptides unique to the heavy and light chain variable regions were predicted by in silico digestion of alemtuzumab variable region sequences found in the IMGT database (http://www.imgt.org/3Dstructure-DB). Alemtuzumab (Campath™, Genzyme, Inc.) was reconstituted to 10 mg/mL in 50 mM ammonium bicarbonate, reduced, alkylated and digested with trypsin (1:20 enzyme: substrate ratio) at 37° C. for 4 hours. Digests were analyzed by IDA LC-ESI-Q-TOF MS. The most abundant peptides matching the in silico list were chosen for subsequent studies.

Figure 5:
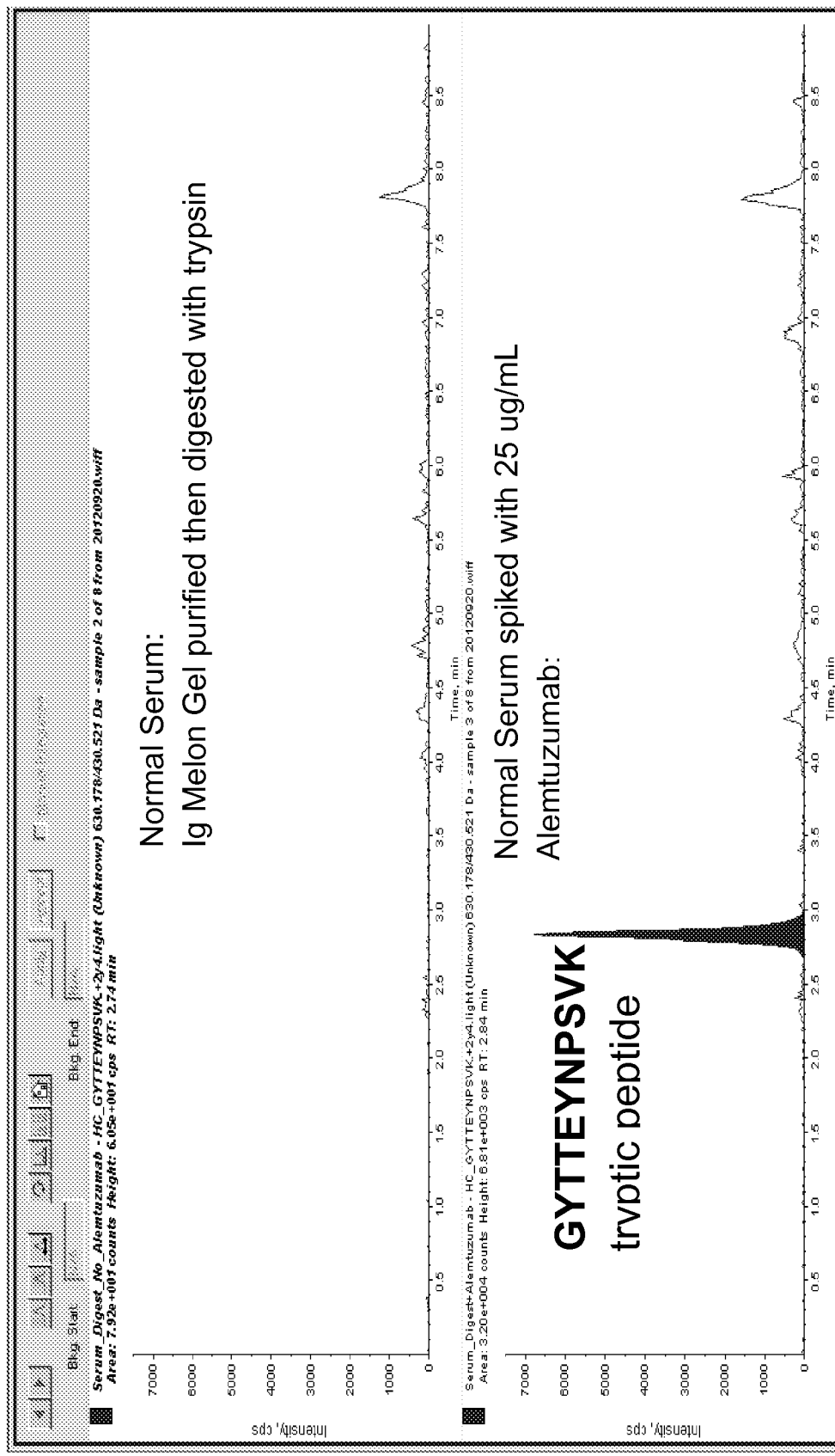
FIG. 5 shows liquid chromatograms of normal human serum after Ig Melon Gel purification and trypsin digest (top graph) and normal human serum spiked with 25 µg/mL alemtuzumab after Ig Melon Gel purification and trypsin digest (bottom graph).

Alemtuzumab was then spiked into normal human serum at a 25 μg/mL level. A dilution series was made from the 25 μg stock. Samples were purified using Melon Gel and digested in a similar manner to Example 1. Identified alemtuzumab tryptic peptides were present in the all spiked samples and no significant amount of the peptides was observed in the normal pooled sera (FIG. 5).

Example 4—Eculizumab

A list of tryptic peptides unique to the heavy and light chain variable regions were predicted by in silico digestion of eculizumab variable region sequences provided by the manufacturer (Alexion). Eculizumab was reconstituted to 10 mg/mL in 50 mM ammonium bicarbonate, reduced, alkylated and digested with trypsin (1:20 enzyme:substrate) at 37° C. for 4 hours. Digests were analyzed by IDA LC-ESI-Q-TOFMS; the most abundant peptides matching the in silico list was chosen for subsequent studies.

Quantitation of eculizumab was accomplished using standard SRM analysis on as described in Example 1 using the horse IgG as an internal digestion standard.

Figure 6:
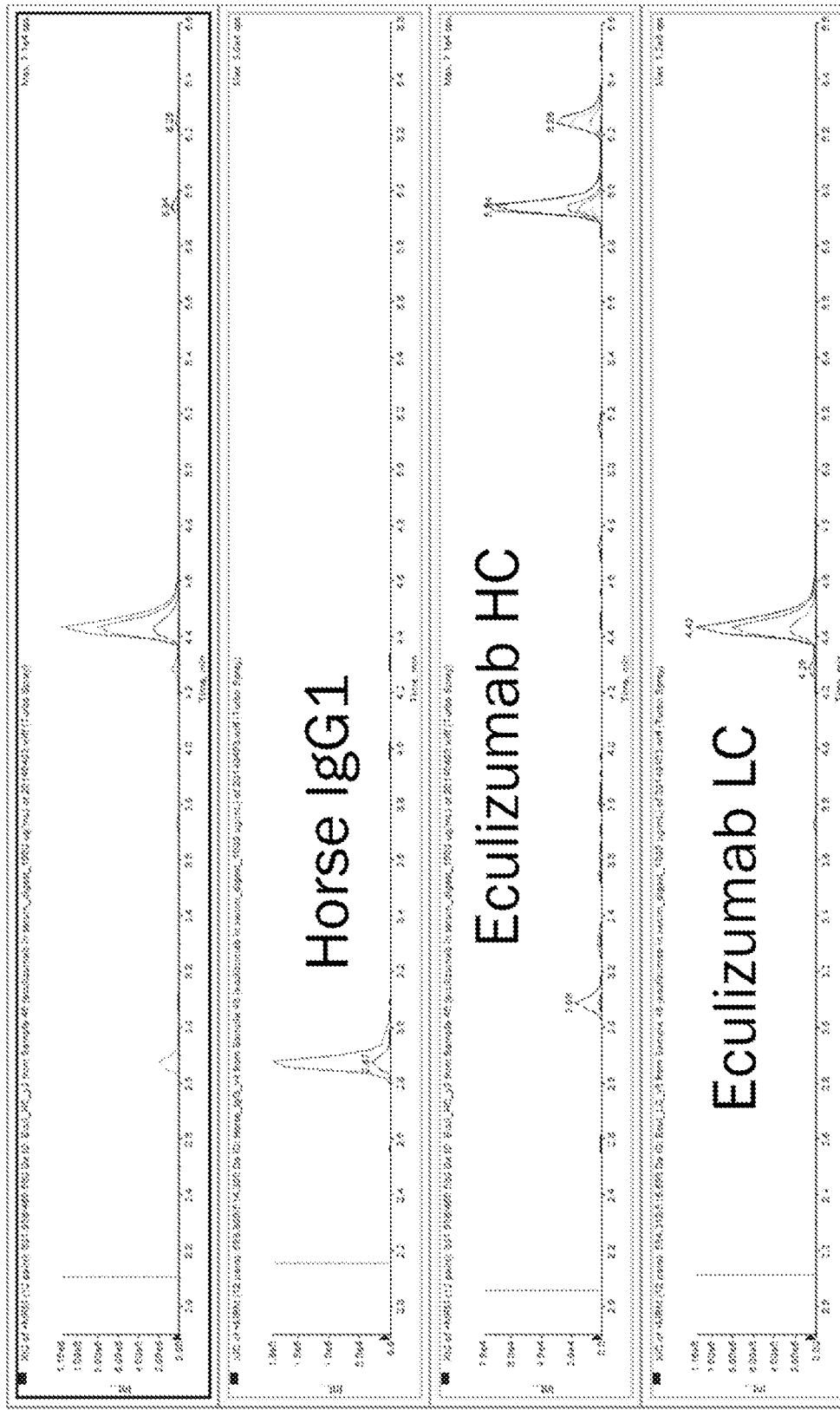
FIG. 6 shows liquid chromatograms used in an SRM analysis for eculizumab. Top graph shows a test sample. Second graph shows a chromatogram of the horse IgG1 standard. Third graph shows a chromatogram of eculizumab heavy chain (HC). Bottom graph shows a chromatogram of eculizumab light chain (LC).
Figure 7:
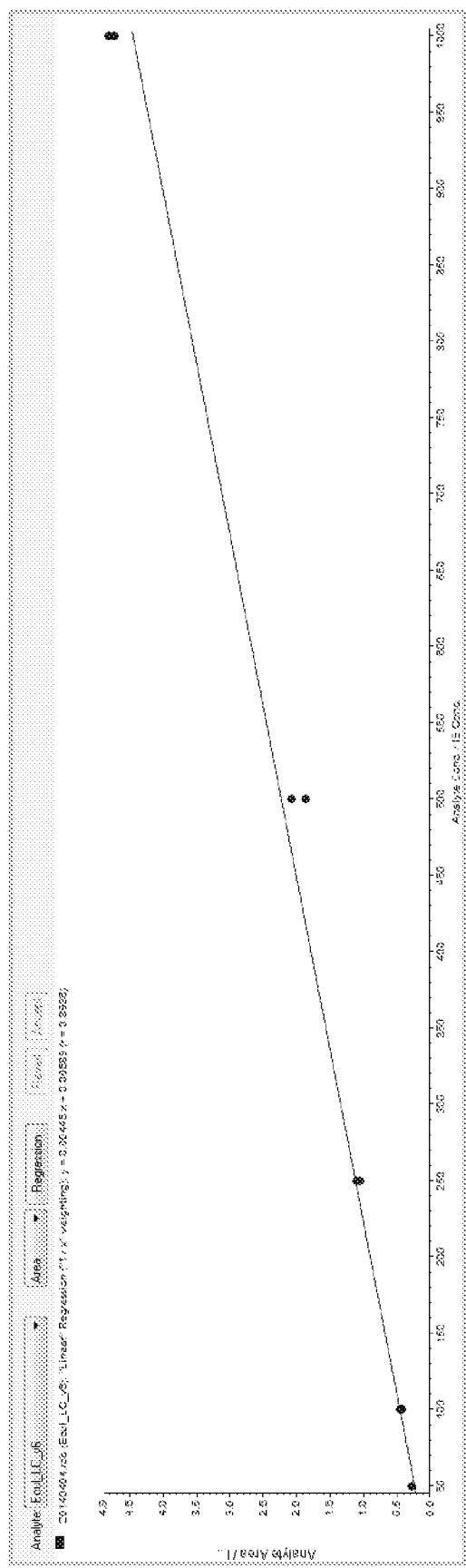
FIG. 7 provides a linear regression graph used to quantify eculizumab in human serum using the area ratio of the light chain to the horse IgG constant region.

Immunoglobulins were isolated by precipitation using a saturated ammonium sulfate solution, followed by trypsin digestion. Peptides were separated on reverse-phase C18 liquid chromatography (Atlantis T3 3×100 mm) and subjected to MS/MS. Exemplary chromatograms for the SRM analysis monitoring for the peptides for horse IgG constant region, and the heavy chain and light chain peptide from eculizumab are shown in FIG. 6. The ability to accurately quantitate the level of infliximab in patient sera was demonstrated by spiking known amounts of infliximab into patient serum and plotting the heavy chain peptide response as a function of drug level (FIG. 7).

Example 5—Comparison with and without Horse IgG

Human serum was spiked with 50 μg of infliximab and the concentration was measured using the method of Example 1. Twenty replicates of the same sample were measured using and the data was either normalized to isotopically labeled peptides internal standards or to a peptide from the constant region of the horse immunoglobulin. The coefficient of variation (CV) for each method was determined for each analysis. The CV's of quantitation using the horse constant region was significantly lower (12% versus 34% for the heavy chain peptide and 8% versus 22% for the light chain peptide) as demonstrated in Table 1.

Example 6—Rituximab

A list of tryptic peptides unique to the heavy and light chain variable regions were predicted by in silico digestion of Rituximab variable region sequences found in the IMGT database (http://www.imgt.org/3Dstructure-DB). Rituximab (Rituxan, Genentech) was reconstituted to 10 mg/mL in 50 mM ammonium bicarbonate, reduced, alkylated and digested with trypsin (1:20 enzyme:substrate) at 37° C. for 4 hours. Digests were analyzed by IDA LC-ESI-Q-TOFMS; the most abundant peptides matching the in silico list were chosen for subsequent studies. A set of tryptic peptides for the rat heavy chain and light chain were identified.

Rituximab was then spiked into normal human serum at 250 mg/ml. A dilution series was made from the stock. Samples were purified using by precipitation in a saturated ammonium sulfate solution and digested according to Example 1. Identified rituximab tryptic peptides were present in the all spiked samples and no appreciable quantities of the peptides were seen in the normal pooled sera (c.f. FIG. 5).

Figure 8:
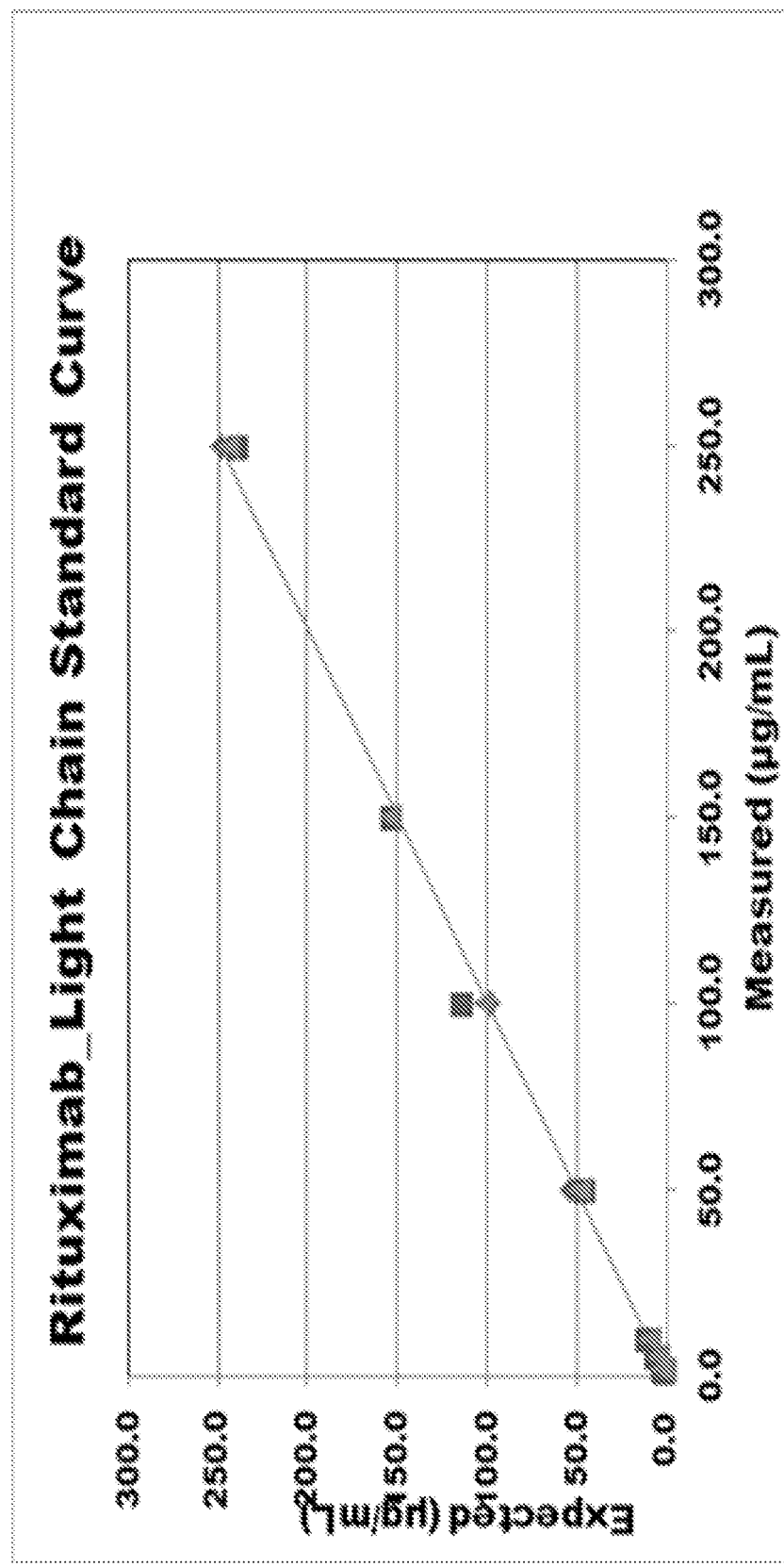
FIG. 8 provides a light chain standard curve for rituximab. Expected concentration (µg/mL) is shown on the y-axis; measured concentration (µg/mL) is shown on the x-axis.

The resulting rituximab light chain standard curve is shown in FIG. 8. Expected concentration (y-axis; μg/mL) correlated with measured concentration (x-axis; μg/mL).

TABLE 1

Comparison of the intra-assay CV of a human serum spiked with infliximab using isotopically labeled peptides versus the horse IgG

| | Heavy Chain | | | | | | | |
|---|---|---|---|---|---|---|---|---|
| | IFX_HC_y4 Analyte Peak Area (counts) | Horse IgG1_LC_y6 IS Peak Area (counts) | Area Ratio | Calculated Concentration (ug/mL) | IFX_HC_y4 Analyte Peak Area (counts) | IFX_HC_ y4 + 13 IS Peak Area (counts) | Area Ratio | Calculated Concentration (ug/mL) |
| Precision_001 | 4.88E+05 | 1.44E+05 | 3.38 | 64.9 | 4.81E+05 | 2.26E+05 | 2.13 | 52.9 |
| Precision_002 | 5.18E+05 | 1.46E+05 | 3.55 | 68.1 | 5.17E+05 | 2.42E+05 | 2.14 | 53 |
| Precision_003 | 4.99E+05 | 1.66E+05 | 3 | 57.7 | 4.96E+05 | 2.12E+05 | 2.34 | 58.1 |
| Precision_004 | 5.27E+05 | 1.35E+05 | 3.91 | 75 | 5.25E+05 | 2.37E+05 | 2.22 | 55 |
| Precision_005 | 5.10E+05 | 1.55E+05 | 3.29 | 63.2 | 5.09E+05 | 2.28E+05 | 2.23 | 55.4 |
| Precision_006 | 4.59E+05 | 1.47E+05 | 3.13 | 60 | 4.54E+05 | 2.35E+05 | 1.94 | 48.1 |
| Precision_007 | 4.45E+05 | 1.56E+05 | 2.85 | 54.8 | 4.44E+05 | 2.36E+05 | 1.88 | 46.6 |
| Precision_008 | 3.98E+05 | 1.62E+05 | 2.46 | 47.2 | 3.95E+05 | 1.68E+05 | 2.35 | 58.2 |
| Precision_009 | 5.07E+05 | 1.68E+05 | 3.01 | 57.8 | 5.05E+05 | 1.88E+05 | 2.69 | 66.5 |
| Precision_010 | 5.34E+05 | 1.56E+05 | 3.43 | 65.7 | 5.29E+05 | 1.72E+05 | 3.08 | 76.2 |
| Precision_011 | 4.46E+05 | 1.66E+05 | 2.68 | 51.6 | 4.42E+05 | 2.15E+05 | 2.06 | 51.1 |
| Precision_012 | 4.50E+05 | 1.67E+05 | 2.7 | 51.9 | 4.45E+05 | 3.15E+05 | 1.41 | 35.2 |
| Precision_013 | 5.04E+05 | 1.55E+05 | 3.26 | 62.6 | 5.01E+05 | 3.43E+05 | 1.46 | 36.4 |
| Precision_014 | 4.69E+05 | 1.49E+05 | 3.15 | 60.4 | 4.66E+05 | 3.39E+05 | 1.38 | 34.3 |
| Precision_015 | 4.99E+05 | 1.75E+05 | 2.86 | 54.9 | 4.98E+05 | 3.22E+05 | 1.55 | 38.5 |
| Precision_016 | 4.56E+05 | 1.66E+05 | 2.75 | 52.8 | 4.53E+05 | 3.35E+05 | 1.35 | 33.8 |
| Precision_017 | 3.89E+05 | 1.43E+05 | 2.72 | 52.2 | 3.88E+05 | 3.45E+05 | 1.13 | 28.2 |
| Precision_018 | 4.79E+05 | 1.70E+05 | 2.82 | 54.2 | 4.75E+05 | 3.80E+05 | 1.25 | 31.2 |
| Precision_019 | 2.87E+05 | 1.12E+05 | 2.57 | 49.4 | 2.84E+05 | 4.70E+05 | 0.605 | 15.4 |
| Precision_020 | 4.36E+05 | 1.59E+05 | 2.74 | 52.6 | 4.33E+05 | 4.42E+05 | 0.978 | 24.6 |
| mean | 4.65E+05 | 1.55E+05 | 3.01E+00 | 57.85 | 4.62E+05 | 2.83E+05 | 1.81E+00 | 44.94 |
| sd | 57888.28 | 14622.53 | 0.369895 | 7.065297 | 57905.55 | 87148.69 | 0.618432 | 15.18757 |
| % CV | 12% | 9% | 12% | 12% | 13% | 31% | 34% | 34% |

| | Light Chain | | | | | | | |
|---|---|---|---|---|---|---|---|---|
| | IFX_LC-y6 Analyte Peak Area (counts) | Horse IgG1_LC_y6 IS Peak Area (counts) | Area Ratio | Calculated Concentration (ug/mL) | IFX_LC_y6 Analyte Peak Area (counts) | IFX_LC_ y6 + 13 IS Peak Area (counts) | Area Ratio | Calculated Concentration (ug/mL) |
| | 1.79E+05 | 1.44E+05 | 1.24 | 66.5 | 1.79E+05 | 2.26E+04 | 7.91 | 55 |
| | 1.89E+05 | 1.46E+05 | 1.3 | 69.4 | 1.89E+05 | 2.55E+04 | 7.42 | 51.6 |
| | 2.02E+05 | 1.66E+05 | 1.22 | 65.3 | 2.02E+05 | 2.37E+04 | 8.54 | 59.3 |
| | 1.86E+05 | 1.35E+05 | 1.38 | 73.9 | 1.86E+05 | 2.44E+04 | 7.62 | 53 |
| | 1.98E+05 | 1.55E+05 | 1.28 | 68.7 | 1.98E+05 | 2.36E+04 | 8.39 | 58.3 |
| | 1.88E+05 | 1.47E+05 | 1.28 | 68.7 | 1.88E+05 | 2.31E+04 | 8.12 | 56.4 |
| | 1.86E+05 | 1.56E+05 | 1.19 | 63.9 | 1.86E+05 | 2.42E+04 | 7.66 | 53.3 |
| | 1.79E+05 | 1.62E+05 | 1.11 | 59.3 | 1.79E+05 | 1.95E+04 | 9.17 | 63.7 |
| | 2.26E+05 | 1.68E+05 | 1.34 | 72 | 2.26E+05 | 1.71E+04 | 13.2 | 91.4 |
| | 2.30E+05 | 1.56E+05 | 1.47 | 79 | 2.29E+05 | 1.81E+04 | 12.7 | 87.9 |
| | 2.04E+05 | 1.66E+05 | 1.23 | 65.9 | 2.04E+05 | 2.27E+04 | 9 | 62.5 |
| | 2.02E+05 | 1.67E+05 | 1.21 | 64.8 | 2.01E+05 | 2.30E+04 | 8.75 | 60.8 |
| | 2.21E+05 | 1.55E+05 | 1.43 | 76.4 | 2.20E+05 | 2.43E+04 | 9.08 | 63.1 |
| | 2.09E+05 | 1.49E+05 | 1.4 | 75.2 | 2.09E+05 | 2.49E+04 | 8.38 | 58.2 |
| | 2.38E+05 | 1.75E+05 | 1.36 | 73 | 2.38E+05 | 2.20E+04 | 10.8 | 74.9 |
| | 2.16E+05 | 1.66E+05 | 1.3 | 69.9 | 2.16E+05 | 2.29E+04 | 9.45 | 65.6 |
| | 1.81E+05 | 1.43E+05 | 1.26 | 67.6 | 1.81E+05 | 2.38E+04 | 7.58 | 52.7 |
| | 2.32E+05 | 1.70E+05 | 1.36 | 73.1 | 2.31E+05 | 2.11E+04 | 10.9 | 75.9 |
| | 1.15E+05 | 1.12E+05 | 1.03 | 55.4 | 1.15E+05 | 2.69E+04 | 4.27 | 29.8 |
| | 1.98E+05 | 1.59E+05 | 1.25 | 66.8 | 1.98E+05 | 2.45E+04 | 8.08 | 56.2 |
| mean | 1.99E+05 | 1.55E+05 | 1.258E+00 | 68.74 | 1.99E+05 | 2.29E+04 | 8.85E+00 | 61.48 |
| sd | 27103.07 | 14622.53 | 0.106009 | 5.702576 | 26932.42 | 2402.077 | 1.952043 | 13.46679 |
| % CV | 14% | 9% | 8% | 8% | 14% | 10% | 22% | 22% |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for quantifying a monoclonal antibody therapeutic in a sample, the method comprising:
    a) providing a human sample comprising a humanized monoclonal antibody therapeutic;
    b) adding an internal standard to the sample, wherein the internal standard is a non-isotopically labeled immunoglobulin from a non-human species; and
    c) subjecting the sample to a mass spectrometry technique to quantify the humanized monoclonal antibody therapeutic in the sample.

2. The method of claim 1, wherein the method further comprises digesting the antibodies in the sample prior to step (c).

3. The method of claim 1, wherein the sample is purified prior to step (c).

4. The method of claim 1, wherein the wherein the mass spectrometry technique comprises a tandem mass spectrometry (MS/MS) technique.

5. The method of claim 1, wherein the mass spectrometry technique comprises an LC-MS/MS technique.

6. A method for quantifying a monoclonal antibody therapeutic in a sample, the method comprising:
    a) providing a human sample comprising a humanized monoclonal antibody therapeutic;
    b) adding an internal standard to the sample, wherein the internal standard is a non-isotopically labeled non-human IgG antibody; and
    c) subjecting the sample to a LC-MS/MS mass spectrometry technique comprising monitoring the non-human IgG antibody constant region to quantify the humanized monoclonal antibody therapeutic in the sample.

7. The method of claim 1, wherein the non-isotopically labeled immunoglobulin is a horse IgG.

8. The method of claim 1, wherein the mass spectrometry technique comprises a liquid chromatography electrospray ionization coupled to a quadrupole mass spectrometry (ESI Triple Quad MS) technique.

9. The method of claim 1, wherein the mass spectrometry technique comprises the use of positive ion mode.

10. The method of claim 1, wherein the mass spectrometry technique comprises selective reaction monitoring (SRM) analysis.

11. The method of claim 1, wherein the SRM analysis comprises monitoring the non-human immunoglobulin constant region.

12. The method of claim 1, wherein the humanized monoclonal antibody therapeutic light chains are decoupled from the humanized monoclonal antibody therapeutic heavy chains prior to step (c).

13. The method of claim 1, wherein quantifying the humanized monoclonal antibody therapeutic in the sample comprises measuring the variable region peptide of the humanized monoclonal antibody therapeutic.

14. The method of claim 1, wherein the sample is a whole blood sample, serum sample, saliva sample, plasma sample, or urine sample.

15. The method of claim 1, wherein the humanized monoclonal antibody therapeutic is selected from the group consisting of: infliximab, alemtuzumab, eculizumab, rituximab and adalimumab.

16. The method of claim 15, wherein the humanized monoclonal antibody therapeutic is infliximab.

17. The method of claim 1, wherein said method can be used to monitor treatment of a disorder treated with said humanized monoclonal antibody therapeutic.

18. The method of claim 17, wherein said disorder is selected from the group consisting of rheumatoid arthritis, psoriatic arthritis, ankylosing spondylitis, Crohn's disease, plaque psoriasis, ulcerative colitis, B-cell chronic lymphocytic leukemia, paroxysmal nocturnal hemoglobinuria (PNH), atypical hemolytic uremic syndrome (aHUS), granulomatosis with polyangiitis (Wegener's granulomatosis), microscopic polyangiitis (MPA), CD-20 positive chronic lymphocytic leukemia, and non-Hodgkin lymphoma.

* * * * *

UNITED STATES PATENT AND TRADEMARK OFFICE
CERTIFICATE OF CORRECTION

PATENT NO. : 10,690,676 B2
APPLICATION NO. : 15/329512
DATED : June 23, 2020
INVENTOR(S) : David R. Barnidge et al.

Page 1 of 1

It is certified that error appears in the above-identified patent and that said Letters Patent is hereby corrected as shown below:

On the Title Page

Column 1 (Assignee), please delete "Roundation" and insert -- Foundation --;

In the Claims

Column 13, Line 26 (Claim 4), please delete "wherein the wherein the" and insert -- wherein the --; therefor.

Signed and Sealed this
First Day of December, 2020

Andrei Iancu
*Director of the United States Patent and Trademark Office*